(12) United States Patent
Sanders et al.

(10) Patent No.: US 9,435,805 B2
(45) Date of Patent: Sep. 6, 2016

(54) **ULTRASENSITIVE DETECTION OF BETA HEMOLYTIC *STREPTOCOCCUS***

(75) Inventors: Mitchell C. Sanders, Northborough, MA (US); Dale Macy, West Boylston, MA (US); Andrei Rakitin, Sudbury, MA (US); Courtney Mankus, Rochdale, MA (US)

(73) Assignee: Woundchek Laboratories (US), Inc., Fall River, MA (US)

( * ) Notice: Subject to any disclaimer, the term of this patent is extended or adjusted under 35 U.S.C. 154(b) by 179 days.

(21) Appl. No.: 13/825,076

(22) PCT Filed: Sep. 22, 2011

(86) PCT No.: PCT/US2011/052716
§ 371 (c)(1),
(2), (4) Date: Mar. 19, 2013

(87) PCT Pub. No.: WO2012/040434
PCT Pub. Date: Mar. 29, 2012

(65) Prior Publication Data
US 2014/0220589 A1     Aug. 7, 2014

Related U.S. Application Data

(60) Provisional application No. 61/385,961, filed on Sep. 23, 2010.

(51) Int. Cl.
*G01N 33/569* (2006.01)
*C12Q 1/04* (2006.01)
*C12Q 1/37* (2006.01)
*G01N 33/558* (2006.01)

(52) U.S. Cl.
CPC ........... *G01N 33/56944* (2013.01); *C12Q 1/04* (2013.01); *C12Q 1/37* (2013.01); *G01N 33/558* (2013.01)

(58) Field of Classification Search
None
See application file for complete search history.

(56) References Cited

U.S. PATENT DOCUMENTS 6,030,835 A * 2/2000 Musser et al. ................ 435/340
2007/0275423 A1* 11/2007 Sebastian et al. ........... 435/7.71
(Continued)

FOREIGN PATENT DOCUMENTS

FR     2886312 A1    12/2006
WO    03063693 A2    8/2003
(Continued)

OTHER PUBLICATIONS

R.E. O'Loughlin et al., "The Epidemiology of Invasive Group A Streptococcal Infection and Potential Vaccine implications: United States, 2000-2004," Clinical Infectious Diseases, vol. 45, No. 7, Oct. 1, 2007, pp. 853-862.
PCT International Search Report dated May 6, 2012 (7 pages).

*Primary Examiner* — Rebecca Martinez
(74) *Attorney, Agent, or Firm* — McDonnell Boehnen Hulbert & Berghoff LLP

(57) ABSTRACT

The present invention is directed to a method for the ultrasensitive detection of beta hemolytic *Streptococcus*, a bacterium implicated in strep throat, using a specific protease marker. Also disclosed is a device as well as a biosensor, both of which are useful for the detection of beta hemolytic *Streptococcus*. The biosensor and the device can be used in conjunction with other reagents as part of a kit for detecting strep throat.

30 Claims, 9 Drawing Sheets

(56) References Cited

U.S. PATENT DOCUMENTS

2008/0145843 A1* 6/2008 Song .................................. 435/6
2009/0232702 A1* 9/2009 Wu et al. ........................ 422/56

FOREIGN PATENT DOCUMENTS

| WO | 2005042770 A2 | 5/2005 |
| WO | 2008075214 A1 | 6/2008 |

* cited by examiner

EDANS-FLVMFLSGK-DABCYL – SEQ.ID.NO.: 4
EDANS-ALVMFLSGK-DABCYL - SEQ.ID.NO.: 5
EDANS-FAVMFLSGK-DABCYL - SEQ.ID.NO.: 6
EDANS-FLAMFLSGK-DABCYL - SEQ.ID.NO.: 7
EDANS-FLVMFLAGK-DABCYL - SEQ.ID.NO.: 8
EDANS-FLVMFLSAK-DABCYL - SEQ.ID.NO.: 9
EDANS-FLVMFLSGA-DABCYL - SEQ.ID.NO.: 10
EDANS-FLVMFLSGK-DABCYL - SEQ.ID.NO.: 11
EDANS-FFVMFLSGK-DABCYL - SEQ.ID.NO.: 12
EDANS-FLFMFLSGK-DABCYL - SEQ.ID.NO.: 13
EDANS-FLVMFLFGK-DABCYL - SEQ.ID.NO.: 14
EDANS-FLVMFLSFK-DABCYL - SEQ.ID.NO.: 15
EDANS-FLVMFLSGF-DABCYL - SEQ.ID.NO.: 16
EDANS-RLVMFLSGK-DABCYL - SEQ.ID.NO.: 17
EDANS-FRVMFLSGK-DABCYL - SEQ.ID.NO.: 18
EDANS-FLRMFLSGK-DABCYL - SEQ.ID.NO.: 19
EDANS-FLVMFLRGK-DABCYL - SEQ.ID.NO.: 20
EDANS-FLVMFLSRK-DABCYL - SEQ.ID.NO.: 21
EDANS-FLVMFLSGR-DABCYL - SEQ.ID.NO.: 22
EDANS-ELVMFLSGK-DABCYL - SEQ.ID.NO.: 23
EDANS-FEVMFLSGK-DABCYL - SEQ.ID.NO.: 24
EDANS-FLEMFLSGK-DABCYL - SEQ.ID.NO.: 25
EDANS-FLVMFLEGK-DABCYL - SEQ.ID.NO.: 26
EDANS-FLVMFLSEK-DABCYL - SEQ.ID.NO.: 27
EDANS-FLVMFLSGE-DABCYL - SEQ.ID.NO.: 28

FIG. 4

| SEQ.ID.NO.: | PEPTIDE | STREP (RFU) | STREP (RFU) | AVG (RFU) | ST DEV (RFU) |
|---|---|---|---|---|---|
| 28 | FLVMFLSGE | 1396 | 1129 | 1262.5 | 188.8 |
| 29 | FFVMFLSG | 377 | 319 | 348.0 | 41.0 |
| 10 | FLVMFLSGA | 423 | 353 | 388.0 | 49.5 |
| 30 | FLEMFLSG | 2647 | 2270 | 2458.5 | 266.6 |
| 31 | FLVMFFLEG | 1233 | 933 | 1083.0 | 212.1 |
| 32 | FLVMFLSR | 182 | 365 | 273.5 | 129.4 |
| 33 | RLVMFLSG | 667 | 647 | 657.0 | 14.1 |
| 34 | FLFMFLSG | 477 | 469 | 473.0 | 5.7 |
| 35 | FRVMFLSG | 882 | 1148 | 1015.0 | 188.1 |
| 36 | FLRMFLSG | 240 | 345 | 292.5 | 74.2 |
| 37 | FAVMFLSG | 571 | 192 | 381.5 | 268.0 |
| 38 | FLVMFLFG | 0 | 483 | 241.5 | 341.5 |
| 39 | FLVMFLRG | 67.6 | 886 | 476.8 | 578.7 |
| 40 | FLVMFLSA | 461 | 0 | 230.5 | 326.0 |
| 16 | FLVMFLSGF | 0 | 303 | 151.5 | 214.3 |
| 41 | FLVMFLAG | 320 | 127 | 223.5 | 136.5 |
| 22 | FLVMFLSGR | 241 | 225 | 233.0 | 11.3 |
| 42 | FLAMFLSG | 0 | 282 | 141.0 | 199.4 |
| 1 | FLVMFLSG | 500 | 531 | 515.5 | 21.9 |
| 43 | ELVMFLSG | 4038 | 3903 | 3970.5 | 95.5 |
| 44 | FLVMFLSG | 92.2 | 214 | 153.1 | 86.1 |
| 45 | FLVMFLSF | 210 | 249 | 229.5 | 27.6 |
| 46 | FLVMFLSE | 745 | 626 | 685.5 | 84.1 |
| 47 | ALVMFLSG | 516 | 358 | 437.0 | 111.7 |
| 48 | FEVMFLSG | 6332 | 6284 | 6308.0 | 33.9 |

FIG. 5

| SEQ.ID.NO.: | PEPTIDE | STREP (RFU) | STREP (RFU) | AVG (RFU) | ST DEV (RFU) |
|---|---|---|---|---|---|
| 28 | FLVMFLSGE | 1756 | 1575 | 1665.5 | 128.0 |
| 30 | FLEMFLSG | 4175 | 5295 | 4735.0 | 792.0 |
| 31 | FLVMFFLEG | 1086 | 1086 | 1086.0 | 0.0 |
| 43 | ELVMFLSG | 8106 | 8388 | 8247.0 | 199.4 |
| 48 | FEVMFLSG | 7795 | 8226 | 8010.5 | 304.8 |
| | PEPTIDE | NEG SWAB (RFU) | NEG SWAB (RFU) | AVG (RFU) | ST DEV (RFU) |
| 28 | FLVMFLSGE | 17.8 | 760 | 388.9 | 524.8 |
| 30 | FLEMFLSG | 590 | 0 | 295.0 | 417.2 |
| 31 | FLVMFFLEG | 0 | 46.6 | 23.3 | 33.0 |
| 43 | ELVMFLSG | 0 | 0 | 0.0 | 0.0 |
| 48 | FEVMFLSG | 448 | 98.6 | 273.3 | 247.1 |

FIG. 6

| SEQ.ID.NO.: | PEPTIDE | STREP (RFU) | NEG SWAB (RFU) |
|---|---|---|---|
| 28 | FLVMFLSGE | 1665.5 | 388.9 |
| 30 | FLEMFLSG | 4735.0 | 295 |
| 31 | FLVMFFLEG | 1086.0 | 23.3 |
| 43 | ELVMFLSG | 8247.0 | 0 |
| 48 | FEVMFLSG | 8010.5 | 273.3 |

FIG. 7

A. 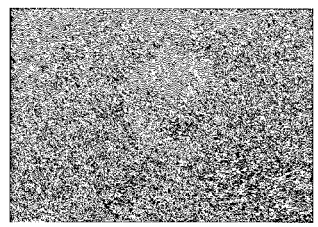 B. 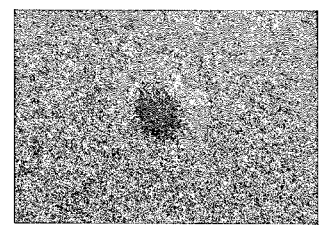
FIG. 9

SEQUENCE LISTING

<160> NUMBER OF SEQ ID NOS: 48

<210> SEQ ID NO 1
<211> LENGTH: 8
<212> TYPE: PRT
<213> ORGANISM: Artificial Sequence
<220> FEATURE:
<223> OTHER INFORMATION: synthetic peptide

<400> SEQUENCE: 1

Phe Leu Val Met Phe Leu Ser Gly
1               5

<210> SEQ ID NO 2
<211> LENGTH: 10
<212> TYPE: PRT
<213> ORGANISM: Artificial Sequence
<220> FEATURE:
<223> OTHER INFORMATION: synthetic peptide

<400> SEQUENCE: 2

Ile Leu Phe Thr Leu Thr Gly Cys Val Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: synthetic peptide

<400> SEQUENCE: 3

Gly Ser Asn Met Tyr Val Tyr Asn Ile Ser
1               5                   10

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Phe Leu Val Met Phe Leu Ser Gly Lys
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic peptide

<400> SEQUENCE: 5

Ala Leu Val Met Phe Leu Ser Gly Lys
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic peptide

<400> SEQUENCE: 6

Phe Ala Val Met Phe Leu Ser Gly Lys
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Phe Leu Ala Met Phe Leu Ser Gly Lys
1               5

<210> SEQ ID NO 8

```
<211> LENGTH: 9
<212> TYPE: PRT
<213> ORGANISM: Artificial Sequence
<220> FEATURE:
<223> OTHER INFORMATION: synthetic peptide

<400> SEQUENCE: 8

Phe Leu Val Met Phe Leu Ala Gly Lys
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic peptide

<400> SEQUENCE: 9

Phe Leu Val Met Phe Leu Ser Ala Lys
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic peptide

<400> SEQUENCE: 10

Phe Leu Val Met Phe Leu Ser Gly Ala
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic peptide

<400> SEQUENCE: 11

Phe Leu Val Met Phe Leu Ser Gly Lys
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic peptide

<400> SEQUENCE: 12

Phe Phe Val Met Phe Leu Ser Gly Lys
1               5

<210> SEQ ID NO 13
<211> LENGTH: 9
<212> TYPE: PRT
<213> ORGANISM: Artificial Sequence
<220> FEATURE:
<223> OTHER INFORMATION: synthetic peptide

<400> SEQUENCE: 13

Phe Leu Phe Met Phe Leu Ser Gly Lys
1               5

<210> SEQ ID NO 14
<211> LENGTH: 9
```

```
<212> TYPE: PRT
<213> ORGANISM: Artificial Sequence
<220> FEATURE:
<223> OTHER INFORMATION: synthetic peptide

<400> SEQUENCE: 14

Phe Leu Val Met Phe Leu Phe Gly Lys
1               5

<210> SEQ ID NO 15
<211> LENGTH: 9
<212> TYPE: PRT
<213> ORGANISM: Artificial Sequence
<220> FEATURE:
<223> OTHER INFORMATION: synthetic peptide

<400> SEQUENCE: 15

Phe Leu Val Met Phe Leu Ser Phe Lys
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic peptide

<400> SEQUENCE: 16

Phe Leu Val Met Phe Leu Ser Gly Phe
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic peptide

<400> SEQUENCE: 17

Arg Leu Val Met Phe Leu Ser Gly Lys
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic peptide

<400> SEQUENCE: 18

Phe Arg Val Met Phe Leu Ser Gly Lys
1               5

<210> SEQ ID NO 19
<211> LENGTH: 9
<212> TYPE: PRT
<213> ORGANISM: Artificial Sequence
<220> FEATURE:
<223> OTHER INFORMATION: synthetic peptide

<400> SEQUENCE: 19

Phe Leu Arg Met Phe Leu Ser Gly Lys
1               5

<210> SEQ ID NO 20
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 20

Phe Leu Val Met Phe Leu Arg Gly Lys
1               5

<210> SEQ ID NO 21
<211> LENGTH: 9
<212> TYPE: PRT
<213> ORGANISM: Artificial Sequence
<220> FEATURE:
<223> OTHER INFORMATION: synthetic peptide

<400> SEQUENCE: 21

Phe Leu Val Met Phe Leu Ser Arg Lys
1               5

<210> SEQ ID NO 22
<211> LENGTH: 9
<212> TYPE: PRT
<213> ORGANISM: Artificial Sequence
<220> FEATURE:
<223> OTHER INFORMATION: synthetic peptide

<400> SEQUENCE: 22

Phe Leu Val Met Phe Leu Ser Gly Arg
1               5

<210> SEQ ID NO 23
<211> LENGTH: 9
<212> TYPE: PRT
<213> ORGANISM: Artificial Sequence
<220> FEATURE:
<223> OTHER INFORMATION: synthetic peptide

<400> SEQUENCE: 23

Glu Leu Val Met Phe Leu Ser Gly Lys
1               5

<210> SEQ ID NO 24
<211> LENGTH: 9
<212> TYPE: PRT
<213> ORGANISM: Artificial Sequence
<220> FEATURE:
<223> OTHER INFORMATION: synthetic peptide

<400> SEQUENCE: 24

Phe Glu Val Met Phe Leu Ser Gly Lys
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic peptide

<400> SEQUENCE: 25

Phe Leu Glu Met Phe Leu Ser Gly Lys
1               5

<210> SEQ ID NO 26
<211> LENGTH: 9
<212> TYPE: PRT
<213> ORGANISM: Artificial Sequence
```

-continued

<220> FEATURE:
<223> OTHER INFORMATION: synthetic peptide

<400> SEQUENCE: 26

Phe Leu Val Met Phe Leu Glu Gly Lys
1               5

<210> SEQ ID NO 27
<211> LENGTH: 9
<212> TYPE: PRT
<213> ORGANISM: Artificial Sequence
<220> FEATURE:
<223> OTHER INFORMATION: synthetic peptide

<400> SEQUENCE: 27

Phe Leu Val Met Phe Leu Ser Glu Lys
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic peptide

<400> SEQUENCE: 28

Phe Leu Val Met Phe Leu Ser Gly Glu
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic peptide

<400> SEQUENCE: 29

Phe Phe Val Met Phe Leu Ser Gly
1               5

<210> SEQ ID NO 30
<211> LENGTH: 8
<212> TYPE: PRT
<213> ORGANISM: Artificial Sequence
<220> FEATURE:
<223> OTHER INFORMATION: synthetic peptide

<400> SEQUENCE: 30

Phe Leu Glu Met Phe Leu Ser Gly
1               5

<210> SEQ ID NO 31
<211> LENGTH: 9
<212> TYPE: PRT
<213> ORGANISM: Artificial Sequence
<220> FEATURE:
<223> OTHER INFORMATION: synthetic peptide

<400> SEQUENCE: 31

Phe Leu Val Met Phe Phe Leu Glu Gly
1               5

<210> SEQ ID NO 32
<211> LENGTH: 8
<212> TYPE: PRT
<213> ORGANISM: Artificial Sequence
<220> FEATURE:

<223> OTHER INFORMATION: synthetic peptide

<400> SEQUENCE: 32

Phe Leu Val Met Phe Leu Ser Arg
1               5

<210> SEQ ID NO 33
<211> LENGTH: 8
<212> TYPE: PRT
<213> ORGANISM: Artificial Sequence
<220> FEATURE:
<223> OTHER INFORMATION: synthetic peptide

<400> SEQUENCE: 33

Arg Leu Val Met Phe Leu Ser Gly
1               5

<210> SEQ ID NO 34
<211> LENGTH: 8
<212> TYPE: PRT
<213> ORGANISM: Artificial Sequence
<220> FEATURE:
<223> OTHER INFORMATION: synthetic peptide

<400> SEQUENCE: 34

Phe Leu Phe Met Phe Leu Ser Gly
1               5

<210> SEQ ID NO 35
<211> LENGTH: 8
<212> TYPE: PRT
<213> ORGANISM: Artificial Sequence
<220> FEATURE:
<223> OTHER INFORMATION: synthetic peptide

<400> SEQUENCE: 35

Phe Arg Val Met Phe Leu Ser Gly
1               5

<210> SEQ ID NO 36
<211> LENGTH: 8
<212> TYPE: PRT
<213> ORGANISM: Artificial Sequence
<220> FEATURE:
<223> OTHER INFORMATION: synthetic peptide

<400> SEQUENCE: 36

Phe Leu Arg Met Phe Leu Ser Gly
1               5

<210> SEQ ID NO 37
<211> LENGTH: 8
<212> TYPE: PRT
<213> ORGANISM: Artificial Sequence
<220> FEATURE:
<223> OTHER INFORMATION: synthetic peptide

<400> SEQUENCE: 37

Phe Ala Val Met Phe Leu Ser Gly
1               5

<210> SEQ ID NO 38
<211> LENGTH: 8
<212> TYPE: PRT
<213> ORGANISM: Artificial Sequence
<220> FEATURE:
<223> OTHER INFORMATION: synthetic peptide

```
<400> SEQUENCE: 38

Phe Leu Val Met Phe Leu Phe Gly
1               5

<210> SEQ ID NO 39
<211> LENGTH: 8
<212> TYPE: PRT
<213> ORGANISM: Artificial Sequence
<220> FEATURE:
<223> OTHER INFORMATION: synthetic peptide

<400> SEQUENCE: 39

Phe Leu Val Met Phe Leu Arg Gly
1               5

<210> SEQ ID NO 40
<211> LENGTH: 8
<212> TYPE: PRT
<213> ORGANISM: Artificial Sequence
<220> FEATURE:
<223> OTHER INFORMATION: synthetic peptide

<400> SEQUENCE: 40

Phe Leu Val Met Phe Leu Ser Ala
1               5

<210> SEQ ID NO 41
<211> LENGTH: 8
<212> TYPE: PRT
<213> ORGANISM: Artificial Sequence
<220> FEATURE:
<223> OTHER INFORMATION: synthetic peptide

<400> SEQUENCE: 41

Phe Leu Val Met Phe Leu Ala Gly
1               5

<210> SEQ ID NO 42
<211> LENGTH: 8
<212> TYPE: PRT
<213> ORGANISM: Artificial Sequence
<220> FEATURE:
<223> OTHER INFORMATION: synthetic peptide

<400> SEQUENCE: 42

Phe Leu Ala Met Phe Leu Ser Gly
1               5

<210> SEQ ID NO 43
<211> LENGTH: 8
<212> TYPE: PRT
<213> ORGANISM: Artificial Sequence
<220> FEATURE:
<223> OTHER INFORMATION: synthetic peptide

<400> SEQUENCE: 43

Glu Leu Val Met Phe Leu Ser Gly
1               5
```

```
<210> SEQ ID NO 44
<211> LENGTH: 8
<212> TYPE: PRT
<213> ORGANISM: Artificial Sequence
<220> FEATURE:
<223> OTHER INFORMATION: synthetic peptide

<400> SEQUENCE: 44

Phe Leu Val Met Phe Leu Ser Gly
1               5

<210> SEQ ID NO 45
<211> LENGTH: 8
<212> TYPE: PRT
<213> ORGANISM: Artificial Sequence
<220> FEATURE:
<223> OTHER INFORMATION: synthetic peptide

<400> SEQUENCE: 45

Phe Leu Val Met Phe Leu Ser Phe
1               5

<210> SEQ ID NO 46
<211> LENGTH: 8
<212> TYPE: PRT
<213> ORGANISM: Artificial Sequence
<220> FEATURE:
<223> OTHER INFORMATION: synthetic peptide

<400> SEQUENCE: 46

Phe Leu Val Met Phe Leu Ser Glu
1               5

<210> SEQ ID NO 47
<211> LENGTH: 8
<212> TYPE: PRT
<213> ORGANISM: Artificial Sequence
<220> FEATURE:
<223> OTHER INFORMATION: synthetic peptide

<400> SEQUENCE: 47

Ala Leu Val Met Phe Leu Ser Gly
1               5

<210> SEQ ID NO 48
<211> LENGTH: 8
<212> TYPE: PRT
<213> ORGANISM: Artificial Sequence
<220> FEATURE:
<223> OTHER INFORMATION: synthetic peptide

<400> SEQUENCE: 48

Phe Glu Val Met Phe Leu Ser Gly
1               5
```

ULTRASENSITIVE DETECTION OF BETA HEMOLYTIC *STREPTOCOCCUS*

RELATED APPLICATION

This application claims the benefit of U.S. Provisional Application No. 61/385,961, filed on Sep. 23, 2010. The entire teachings of the above application are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
a) Filename: 32651028001Sequencelisting.txt, created Sep. 22, 2011, 8.31 KB in size.

REFERENCE TO A "SEQUENCE LISTING"

The sequence listing submitted via EFS, in compliance with 37 CFR §1.52(e)(5), is incorporated herein by reference. The sequence listing text file submitted via EFS contains the file "98282-000121_Substitute_ST25", created on Aug. 21, 2013, which is 9.20 KB in size.

BACKGROUND OF THE INVENTION

Beta hemolytic *Streptococcus*, the causative agent of strep throat, is one of the most common ailments of children from 5 to 18 years of age. Current estimates indicate that in the United States alone there are 7.5 million cases of strep throat and over 25 million cases of sore throat. Doctor's visits for sore throats are a major burden on the pediatric health care system and considerable time is lost from work by parents that may spend an entire day at home for a scheduled visit to the doctor.

Current professional care tests on the market include cultures that can take 1-2 days and rapid tests that are based on antibodies and lateral flow technologies.

Current professional care rapid tests do not have applicability for consumer use for several reasons: (1) antibody-based tests have very poor sensitivity because it is difficult to collect the swab sample at the wound site at the back of the inflamed tonsils; (2) presenting a swab at the back of the throat is a choking risk for a child; and (3) many antibody-based tests are too kit-like and have too many steps for the consumer to properly follow instructions. As a result, there is considerable demand and unmet need for a sensitive consumer diagnostic test for strep throat.

The presence of β-hemolytic Streptococci (also known as group A Streptococci or *Streptococcus pyogenes*) in wounds causes infection and prevents healing at levels significantly lower than the $10^6$ bacteria per gram of tissue that is often considered the level leading to infection (see Steed, David L et al. *Guidelines for the Treatment of Diabetic Ulcers*. Wound Rep Reg. 2006, 14: 680-92; and Edwards, Ruth and Keith G. Harding. *Bacteria and Wound Healing*. Curr Op Infec Dis. 2004, 17: 91-96; the teachings of which are incorporated herein by reference in their entirety). Therefore, the presence of β-hemolytic *Streptococcus* is undesirable at any level and early detection is of the essence in order to avoid the possibility of severe cellulitis, sepsis, or streptococcal toxic shock syndrome (see O'Loughlin, Rosalyn E et al. The Epidemiology of Invasive Group A Streptococcal Infection and Potential Vaccine Implications: United States, 2000-2004. *Clin Infec Dis*. 2007, 45: 853-62; the teachings of which are incorporated herein by reference in their entirety). Thus, there is a need for a simple and rapid assay that can detect low levels of Group A *Streptococcus* organisms, for example, in wounds.

SUMMARY OF THE INVENTION

The present invention relates to a highly sensitive enzyme assay for the detection of strep throat. Using a simple and rapid assay of the present invention, which can be incorporated into wound dressings and diagnostic devices, Group A *Streptococcus* organisms have been detected at levels as low as $10^3$ CFU/mL.

One embodiment of the invention is a device for detecting the presence or absence of a bacterium in a sample, comprising a first amplifier configured to release a substrate in response to an enzyme initiated by (i.e., produced and/or secreted by) the bacterium; and a second amplifier, in fluid communication with the first amplifier, configured to bind to the released substrate and to produce a signal in the presence of the bacterium.

Another embodiment of the invention is a device for detecting the presence or absence of a bacterium in a sample, comprising a) a reaction chamber configured to hold a sample under conditions that result in release of a substrate from the first amplifier in response to an enzyme initiated by a bacterium; b) a membrane incorporated into the chamber; and c) a lateral flow cassette comprising a conjugate pad in fluid communication with the membrane, a lateral flow strip, a wicking pad, and a flow strip chamber; wherein the membrane is configured to allow the sample to flow to the conjugate pad and lateral flow strip under conditions that allow the released substrate to bind to a second amplifier, and wherein the flow strip is configured to produce a signal when the bacterium is present in the sample.

Yet another embodiment of the invention is a device for detecting the presence of a bacterium in a sample, said device comprising a first conjugate capable of being modified by an enzyme produced and/or secreted by the bacterium to release a first amplified signal and a second conjugate for amplifying the first amplified signal to produce a second amplified signal, which when present, indicates the presence of the bacterium in the sample.

One embodiment of the invention is a biosensor for detecting the presence or absence of a bacterium in a sample, the biosensor comprising a solid support and a first amplifier, the first amplifier comprising a peptide comprising an amino acid sequence selected from the group consisting of FLVMFLSG (SEQ. ID. NO.: 1), ILFTLTGCVG (SEQ. ID. NO.: 2) and GSNMYVYNIS (SEQ. ID. NO.: 3) and configured to release the peptide in response to an enzyme initiated by the bacterium.

Another embodiment of the invention is a kit for detecting strep throat, comprising a device according to any one of Claims 1-21 or a biosensor according to any of Claims 22-29, and one or more reagents for detecting the enzyme produced and/or secreted by a bacterium causing said strep throat.

Another embodiment of the invention is an isolated peptide comprising an amino acid sequence selected from the group consisting of FLVMFLSG (SEQ. ID. NO.: 1), ILFTLTGCVG (SEQ. ID. NO.: 2) and GSNMYVYNIS (SEQ. ID. NO.: 3).

One embodiment of the invention is a method for detecting the presence or absence of a bacterium in a sample, the method comprising incubating the sample with a first amplifier, a portion of the first amplifier being released in response to an enzyme initiated by the bacterium; and incubating the released portion of the first amplifier with a second amplifier configured to bind to the released portion and to produce a signal in the presence of the bacterium.

Another embodiment of the invention is method for detecting the presence or absence of a bacterium in a sample using a lateral flow device comprising: a reaction chamber having a membrane; and a lateral flow cassette comprising a conjugate pad in fluid communication with the membrane, a lateral flow strip including a first conjugate, a wicking pad, and a flow strip chamber; the method comprising a) contacting the sample with a first amplifier in the reaction chamber under conditions that result in release of a substrate from the first amplifier in response to an enzyme produced and/or secreted by the bacterium; b) collecting the released substrate onto a second amplifier in the enzyme reaction chamber under conditions that allow the released substrate to bind to the second amplifier; c) allowing the sample to flow from the reaction chamber onto the conjugate pad; and d) detecting the presence of a signal on the flow strip, wherein the presence of the signal indicates the presence of the bacterium in the sample and absence of a signal on the flow strip indicates the absence of the bacterium in the sample.

Yet another embodiment of the invention is a method for detecting the presence or absence of an enzyme in a sample, comprising: a) contacting the sample with a first amplifier under conditions that result in release of a substrate from the first amplifier in response to an enzyme initiated by the bacterium; b) collecting the released substrate onto a second amplifier under conditions that result in binding of the released substrate to the second amplifier, thereby producing a soluble complex; and c) detecting the soluble complex; wherein the presence of the soluble complex indicates the presence of the enzyme in the sample and the absence of the soluble complex indicates the absence of the enzyme in the sample.

BRIEF DESCRIPTION OF THE FIGURES

The foregoing will be apparent from the following more particular description of example embodiments of the invention, as illustrated in the accompanying drawings.

FIG. 4 is a diagnostic peptide array for the detection of strep throat.

FIG. 5 is a table of the relative fluorescence units emitted by exemplary biosensors of the present invention in the presence of *Streptococcus* as a function of peptide sequence in a FRET-based assay.

FIG. 6 is a table of the relative fluorescence units emitted by exemplary biosensors of the present invention in the presence or absence of *Streptococcus* as a function of peptide sequence in a FRET-based assay.

FIG. 7 is a table of the relative fluorescence units emitted by exemplary biosensors of the present invention in the presence or absence of *Streptococcus* as a function of peptide sequence in a FRET-based assay.

FIG. 9 is an example of a transpiration membrane or filter.

DETAILED DESCRIPTION OF THE INVENTION

Figure 1:
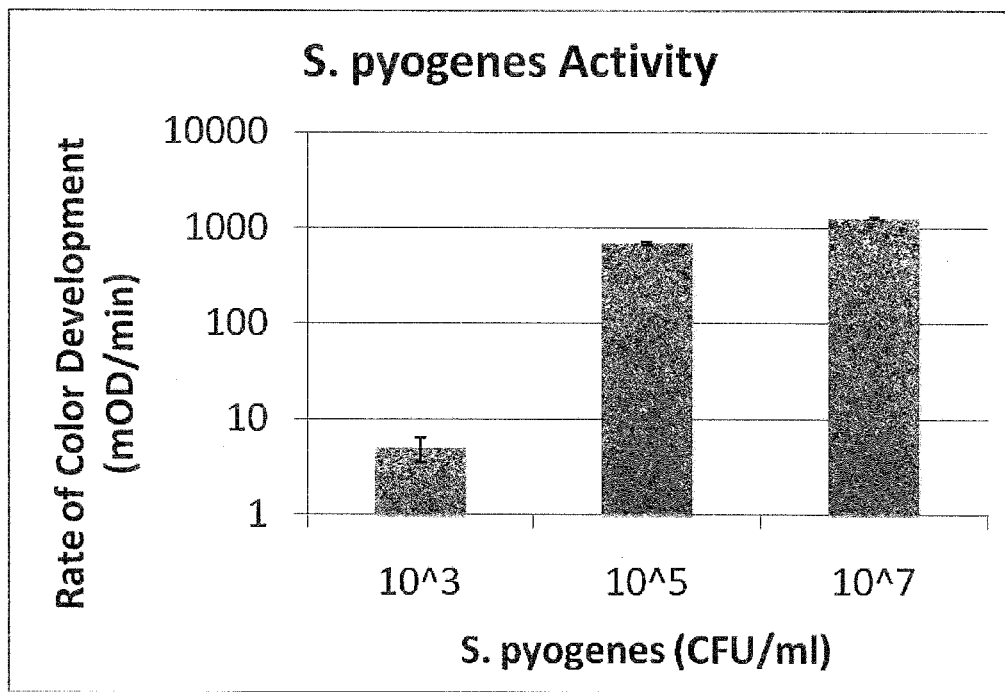
FIG. 1 is a plot of *S. pyogenes* concentration (CFU/mL) versus the rate of color development (mOD/min).

As used in the description of this invention, the terms set forth below have the following definitions.

As used herein, the singular forms "a", "an" and "the" include plural referents unless the context clearly dictates otherwise. Thus, for example, reference to "substrate" can include a plurality of substrates. Further, the plurality can comprise more than one of the same substrate or a plurality of different substrates.

As part of their normal growth processes, many microorganisms, such as bacteria, secrete a number of enzymes into their growth environment. These enzymes have numerous functions including, but not limited to, the release of nutrients, protection against host defenses, cell envelope synthesis (in bacteria) and/or maintenance, and others as yet undetermined. Many microorganisms also produce enzymes on their cell surface that are exposed to (and interact with) the extracellular environment. Many of these enzymes are specific to the microorganism that secretes them, and as such, can serve as specific markers for the presence of those microorganisms. A system that can detect the presence of these enzymes that are produced and/or secreted can serve to indicate the presence of the producing/secreting microorganism. Alternatively, a system that can detect the absence of these enzymes that are produced and/or secreted can serve to indicate the absence of the producing/secreting microorganism. Such a detection system is useful for detecting or diagnosing an infection, for example, a strep infection.

A microorganism detection system, as described herein, can be tailored to detect one specific microorganism, such as *Streptococcus pyogenes*, by identifying a protein such as a secreted enzyme specific to the microorganism to be detected. Alternatively, a test system can be designed to simultaneously identify more than one microorganism species (for example, at least 2, at least 5, or at least 10 different microorganism species), such as those that commonly infect wounds. Identifying those enzymes that are common to certain classes of pathogenic microorganisms, but which are not present in non-pathogenic microorganisms is one way to achieve this goal. Such enzymes can be identified, for example, with a computer based bioinformatics screen of microbial genomic databases. By using enzymes as the basis for detection systems, sensitive tests can be designed, since even a very small amount of enzyme can catalyze the turnover of a substantial amount of substrate, resulting in signal amplification.

The presence of a pathogenic bacterium can be detected by designing a synthetic substrate that will specifically react with an enzyme that is present on the surface of the cell or secreted by the cell. These synthetic substrates can be labeled with a detectable label that, upon reaction with a specific enzyme, undergo an observable modification, for example, a visible color change.

Examples of pathogenic bacteria include, but are not limited to those disclosed in U.S. Patent Publication 2005/0142622, the contents of which are incorporated herein by reference in their entirety. Examples of *streptococcus* include, but are not limited to, *Streptococcus pyogenes, Streptococcus pneumoniae,* or *Streptococcus agalactiae.* Examples of strep throat-specific bacteria include, but are not limited to *Streptococcus pyogenes*, which is the causative agent of strep throat as well as many other types of infections, including wound infections. It is a very common pathogen found in chronic would infections.

The enzyme can be any hydrolysis enzyme that produces a modified (e.g., soluble, released) substrate. For example, the enzyme can be a lysin (an enzyme that functions to lyse host cells); a cell wall enzyme (an enzyme involved in the synthesis and turnover of bacterial cell wall components, including peptidoglycan), a protease (an enzyme that specifically or non-specifically cleaves a peptide, polypeptide, or protein), a hydrolase (an enzyme that breaks down polymeric molecules into their subunits), a metabolic enzyme (an enzyme designed to perform various housekeeping functions of the cell, such as breaking down nutrients into components that are useful to the cell), or a virulence enzyme (an enzyme that is required by the bacterial cell to cause an infection). In some preferred embodiments, the enzyme is a protease. Examples of enzymes include, but are not limited to, those disclosed in U.S. Patent Publication 2005/0142622, the contents of which are incorporated herein by reference in their entirety Substrates for use in the present invention comprise any molecule, either synthetic or naturally-occurring, that can interact with an enzyme of the present invention. Substrates include those substrates described herein, as well as substrates for those enzymes that are known in the art. Examples of substrates include Alt derived fluorescent peptides, for example, peptides comprising the amino acid sequences FLVMFLSG (SEQ ID NO: 1) (known as H11, which is also part of an *E. faecalis* pheromone), ILFTLTGCVG (SEQ. ID. NO.: 2), GSNMYVYNIS (SEQ. ID. NO.: 3), and the amino acid sequences depicted in any of FIGS. 4-7. H11 was identified in a screen for peptides hydrolyzed by *S. pyogenes*. It was surprising to the inventors that the sequence has been identified as part of an *E. faecalis* pheromone. The inventors know of no evidence that this pheromone would be a target of degradation by a *streptococcus* protease. Substrates for use in the present invention can also comprise fluorescent peptidoglycans, for example, fluorescent-N-acetylglucosamine-1,4-N-acetylmuramic acid, fluorescent-N-acetylmuramyl-L-alanine, or fluorescent-lipoteichoic acid (peptidoglycans over-labeled with fluorescein would be quenched from fluorescing, but following hydrolysis by a pathogen would fluoresce); and a lipid vesicle containing dye for the detection of hemolysin (many hemolysins form ordered protein complexes that are pore forming toxins, and can be detected by the release of dye from a lipid vesicle followed by diffusion of the dye onto a hydrophobic solid substrate). Such substrates described herein can be obtained from commercial sources, e.g., Sigma (St. Louis, Mo.), or can be produced, e.g., isolated or purified, or synthesized using methods known to those of skill in the art.

Substrates with hydrophobic leaving groups can be non-covalently bound to hydrophobic surfaces. Alternatively, hydrophilic or hydrophobic substrates can be covalently coupled to surfaces by disulfide bonds or through amine, carboxyl or hydroxyl groups. Methods for coupling substrates to a solid support are known in the art. For example, fluorescent and chromogenic substrates can be coupled to solid substrates using non-essential reactive termini such as free amines, carboxylic acids or sulfhydryl groups, as long as the coupling does not affect the reaction with the wound pathogens. Free amines can be coupled to carboxyl groups of a substrate using, for example, a 10-fold molar excess of either N-ethyl-N'-(3-dimethylaminopropyl)carbodiimide hydrochloride (EDC) or N-cyclohexyl-N'-2-(4'-methyl-morpholinium)ethyl carbodiimide-p-toluene sulphonate (CMC) for 2 hours at 4° C. in distilled water adjusted to pH 4.5 to stimulate the condensation reaction to form a peptide linkage. Disulfide groups can be reduced with DTT or TCEP and then coupled to a free amino group on a surface with N-e-maleimidocaproic acid (EMCA, Griffith et al., *Febs Lett.* 134:261-263, 1981).

Some examples of substrates for use in the present invention are polypeptides comprising, consisting essentially of, or consisting of one or more of the amino acid sequences: FLVMFLSG (SEQ. ID. NO.: 1), ILFTLTGCVG (SEQ. ID. NO.: 2), GSNMYVYNIS (SEQ. ID. NO.: 3), an amino acid sequence depicted in any of FIGS. 4-7, or a polypeptide having at least 50%, 60%, 70%, 80%, 85%, 90%, 95%, or 99% sequence identity to SEQ ID NO: 1-3 or an amino acid sequence depicted in any of FIGS. 4-7, as determined using a sequence comparison program and parameters described herein. In some embodiments, the peptide substrate comprises an amino acid sequence selected from the group consisting of FLVMFLSG (SEQ. ID. NO.: 1), ILFTLTGCVG (SEQ. ID. NO.: 2) and GSNMYVYNIS (SEQ. ID. NO.: 3). In other embodiments, the peptide substrate can be specific for *S. pyogenes* (e.g., H11). Such polypeptides can be enzymatically cleaved by strep throat-specific proteases, as described herein.

The polypeptides of the invention also encompass fragments and sequence variants of the polypeptides and nucleic acids described above. Variants include a substantially homologous polypeptide encoded by the same genetic locus in an organism, i.e., an allelic variant, as well as other variants. Nucleic acid variants also include allelic variants. Variants also encompass polypeptides or nucleic acids derived from other genetic loci in an organism, but having substantial homology to a polypeptide of SEQ ID NO: 1-3 or an amino acid sequence depicted in any of FIGS. 4-7. Variants also include polypeptides or nucleic acids substantially homologous or identical to these polypeptides or nucleic acids but derived from another organism, i.e., an ortholog. Variants also include polypeptides or nucleic acids that are substantially homologous or identical to these polypeptides or nucleic acids that are produced by chemical synthesis. Variants also include polypeptides or nucleic acids that are substantially homologous or identical to these polypeptides or nucleic acids that are produced by recombinant methods. In some embodiments, the variants are glutamic acid mutants of SEQ. ID. NO.: 1. In some embodiments, the H11 peptide can be substituted with one non polar (e.g., alanine or phenylalanine), basic (e.g., arginine), or acidic (e.g., glutamic acid) residue flanking the mapped cleavage sites of the peptide (M-F and F-L). In some embodiments, the peptides can be synthesized as fluorescence resonance energy transfer (FRET) pairs (e.g., EDANS and DABCYL), which can then be tested with negative and positive *streptococcus* control swabs in order to identify the peptide that has the highest signal to noise ratio. Upon hydrolysis of the peptide, the EDANS dye fluoresces at 490 nm.

The percent identity of two amino acid sequences or two nucleic acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., percent identity=number of identical positions/total number of positions×100). In certain embodiments, the length of the amino acid sequence aligned for comparison purposes is at least 30%, preferably, at least 40%, more preferably, at least 60%, and even more preferably, at least 70%, 80%, 90%, or 100% of the length of the reference sequence. The actual comparison of the two sequences can be accomplished by well-known methods, for example, using a mathematical algorithm. A preferred, non-limiting example of such a mathematical algorithm is described in Karlin et al., *Proc. Natl. Acad. Sci. USA*, 90:5873-5877, 1993). Such an algorithm is incorporated into the BLAST programs (version 2.2) as described in Schaffer et al. (*Nucleic Acids Res.*, 29:2994-3005, 2001). When utilizing BLAST and Gapped BLAST programs, the default parameters of the respective programs can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

In another embodiment, the percent identity between two amino acid sequences or two nucleic acid sequences can be accomplished using the GAP program in the GCG software package (Accelrys Inc., San Diego, Calif.) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (Accelrys Inc.), using a gap weight of 50 and a length weight of 3.

The invention also encompasses polypeptides having a lower degree of identity but having sufficient similarity so as to perform one or more of the same functions performed by the polypeptide, e.g., the ability to act as a substrate for a *Streptococcus pyogenes*-specific protease. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247: 1306-1310, 1990).

Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region, such critical regions include the cleavage site for a *Streptococcus pyogenes*-specific protease.

Amino acids in a polypeptide of the present invention that are essential for cleavage by a *Streptococcus pyogenes*-specific protease can be identified by methods known in the art, such as site-directed mutagenesis or alanine-scanning mutagenesis (Cunningham et al., *Science*, 244: 1081-1085, 1989). The latter procedure introduces a single alanine mutation at each of the residues in the molecule (one mutation per molecule).

The invention also includes polypeptide fragments of the amino acid sequence of SEQ ID NO: 1, 2, or 3 or functional variants thereof. The present invention also encompasses fragments of the variants of the polypeptides described herein. Useful fragments include those that retain the ability to act as substrates for a strep throat-specific protease.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The enzymes of the present invention can modify substrates, for example, proteins or polypeptides, by cleavage, and such modification can be detected to determine the presence or absence of a pathogen, such as *Streptococcus pyogenes*, in a sample. One method for detecting modification of a substrate by an enzyme is to label the substrate with two different dyes, where one serves to quench the fluorescence of the other dye by fluorescence energy transfer (FRET) when the molecules, for example, dyes or colorimetric substances are in close proximity, and is measured by detecting changes in fluorescence.

FRET is the process of a distance-dependent excited state interaction in which the emission of one fluorescent molecule is coupled to the excitation of another. A typical acceptor and donor pair for resonance energy transfer consists of 4-[[-(dimethylamino)phenyl]azo]benzoic acid (DABCYL, Dabcyl) and 5-[(2-aminoethylamino]naphthalene sulfonic acid (EDANS, Edans). EDANS is excited by illumination with 336 nm light, and emits a photon with wavelength 490 nm. If a DABCYL moiety is located within 20 angstroms of the EDANS, this photon will be efficiently absorbed. DABCYL and EDANS will be attached to opposite ends of a peptide substrate. If the substrate is intact, FRET will be very efficient. If the peptide has been cleaved by an enzyme, the two dyes will no longer be in close proximity and FRET will be inefficient. The cleavage reaction can be followed by observing either a decrease in the fluorescence of the acceptor or an increase in fluorescence of the donor. An increase in fluorescence of EDANS can be measured at, for example, 485 nm or 538 nm.

If the substrate to be modified is a protein, peptide, or polypeptide, the substrate can be produced using standard recombinant protein techniques (see for example, Ausubel et al., "Current Protocols in Molecular Biology," John Wiley & Sons, (1998), the entire teachings of which are incorporated by reference herein). In addition, the enzymes of the present invention can also be generated using recombinant techniques. Through an ample supply of enzyme or its substrate, the exact site of modification can be determined, and a more specific substrate of the enzyme can be defined, if so desired. This substrate can also be used to assay for the presence of the pathogenic bacteria.

The substrates are labeled with a detectable label that is used to monitor interactions between the enzyme and the substrate and detect any substrate modifications, for example, cleavage of the substrate or label resulting from such interactions. Examples of detectable labels include various dyes that can be incorporated into substrates, for example, affinity tags, spin labels, antigen or epitope tags, haptens, enzyme labels, prosthetic groups, fluorescent materials, chemiluminescent materials, bioluminescent materials, pH-sensitive materials, colorimetric components, and radioactive materials. Examples of suitable enzyme labels include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a chemiluminescent material includes luminol; examples of bioluminescent materials include luciferase, luciferin, and aequorin; and examples of suitable radioactive material include $^{125}$I, $^{131}$I, $^{35}$S, and $^{3}$H. Other examples of detectable labels include Bodipy, Pyrene, Texas Red, IAEDANS, Dansyl Aziridine, IATR and fluorescein. Succimidyl esters, isothiocyanates, and iodoacetamides of these labels are commercially available. When detectable labels are not employed, enzymatic activity can be determined by other suitable methods, for example detection of substrate cleavage through electrophoretic analysis, or other methods known to one skilled in the art.

One example of a preferred detectable label is a chromogenic dye (also referred to herein as a color-producing label) that allows monitoring of the modification (e.g., hydrolysis) of the substrate by the bacterial enzyme. Dyes that produce detectable modification, e.g., a visible color change, are known to those of skill in the art.

Substrates suitably labeled with detectable labels, for example, a chromogenic dye or erioglaucine, and attached or incorporated into a sensor apparatus, can act as indicators of the presence or absence of pathogenic bacteria that produce and/or secrete the aforementioned enzymes. When more than one substrate is utilized, each may be labeled so as to distinguish it from another (for example, using different detectable labels) and/or each may be localized in a particular region on a solid support.

Preferably, the substrate comprises a peptide tethered to a bead. Further, the bead is about 1 micron to about 100 microns in diameter, or about 1 to about 10 microns diameter or about 50 to about 90 microns in diameter. In one embodiment, the peptide includes a detectable label, such as an affinity tag or a color-producing label (e.g., a dye).

The sample in which the presence or absence of bacteria is detected, or an infection is diagnosed, can be, for example, a wound, a body fluid, such as blood, urine, sputum, saliva, or wound fluid. Preferably, the sample is saliva, for example, saliva collected on a swab. The sample can also comprise any article that bacteria may be contained on/in (e.g., a solid support). For example, it can be a wound dressing, a container for holding body fluids, a catheter, a urine collection bag, a chest drain, a blood collection bag, a plasma collection bag, a polymer, a disk, a scope, a toothbrush, a filter, a lens, foam, cloth, paper, a suture, a dipstick, a swab, a test tube, a well of a microplate, contact lens solutions, or a swab from an area of a room or building, for example, an examination room or operating room of a healthcare facility, a bathroom, a kitchen, or a process or manufacturing facility. Due to the high sensitivity of the methods and devices of the invention, the sample need not be obtained from the back of the throat (which can lead to choking). Instead, it can be obtained from the inside of the cheek, for example, between the cheek and lower gums or on the tongue.

Most lateral flow assays that are based on immunodetection of a substrate bound to an antibody-gold conjugate can be very specific (see, e.g., U.S. Pat. Nos. 5,712,172; 7,666,614; 6,979,576; 6,368,828; or 6,194,221). The reaction is driven by the flow of liquid from the conjugate pad, down the lateral flow strip, to the dense wicking pad. The gold conjugate that amplifies the signal is dried to the conjugate pad and, once buffer is applied to the lateral flow strip, the gold is collected through an interaction with an antibody to form a line. These assays are single amplification assays.

However, lateral flow immunoassays do not have the sensitivity of a two-conjugate protease activity assay. A two-conjugate protease activity assay includes two amplification steps, which provide for an increase in sensitivity. An active enzyme, in this case a specific protease from the bacterium *Streptococcus pyogenes*, can be detected through peptide hydrolysis, releases a peptide from a bead, for example, with a dual affinity tag. This is a first amplification. The peptide can be attached to the bead by methods known in the art, such as those described by Gregg Hermanson in *Bioconjugate Techniques* (Second Edition) available from Academic Press, San Diego, Calif., the teachings of which are incorporated herein by reference in their entirety.

In one embodiment, the invention includes a device for detecting the presence of a bacterium in a sample, the device comprising a first amplifier configured to release a peptide substrate in response to an enzyme initiated by the bacterium; and a second amplifier, in fluid communication with the first amplifier, configured to bind to the released peptide to detect the presence of the bacterium. In one embodiment, the invention includes a method for detecting the presence of a bacterium in a sample, the method comprising amplifying the presence of an enzyme initiated by the bacterium by reacting the enzyme with a peptide substrate, a portion of the peptide substrate being released in response to the enzyme; and amplifying the presence of the released peptide substrate by reacting it with a second conjugate to enable detection of the presence of the bacterium.

We previously identified a protease assay-peptide bead conjugate approach for detecting bacteria with broad spectrum peptides CPI2 and PAPA that does not cross-react with host enzymes (see WO2005/042770 and WO2003/063693, the contents of which are incorporated herein by reference in their entirety). Although these peptides detect a number of wound pathogens at ~3×10$^5$ CFU/mL, they are not specific for β-hemolytic *streptococcus* and it is not sensitive enough to have utility as a consumer product, which requires the test to be very sensitive (e.g., not missing any true positives).

The released/clipped peptide (also referred to herein as "modified first conjugate") labeled with the dual affinity tag binds to the second conjugate (such as a gold particle) that can be collected and detected on the surface of a membrane using, for example, passive filtration, tangential flow or lateral flow.

In some instances, the dual affinity tag can be replaced with a colored label such as erioglaucine (Blue dye #1) and the second conjugate omitted. The negative charge of erioglaucine provides a weak attraction to a membrane surface, thereby collecting the dye and providing a color indicator for infection.

One feature of the two-conjugate protease activity assay is that the peptide-labeled bead is preferably large (e.g., greater than about 1 micron) and unable to pass through the membrane while the second conjugate is much smaller (e.g., about 1 to about 5 nm) and readily passes through the membrane to collect on the surface to form a visible line or pattern. Thus, some embodiments include a device for detecting the presence of a bacterial enzyme through the hydrolytic turnover of an enzyme substrate resulting in the first amplification step and the collection of the released substrate onto a second colored conjugate resulting in a second amplification of the colored conjugate onto a membrane surface.

In some embodiments, the peptide used comprises, consists essentially of, consists of a peptide of SEQ. ID. NO.: 1 (also referred to herein, as H11). Based on site mutagenesis of this sequence, the inventors have determined that some amino acid substitutions with glutamic acid (E) either retained or enhanced activity. Other peptides from the screen that have promise include ILFTLTGCVG (SEQ. ID. NO.: 2) and GSNMYVYNIS (SEQ. ID. NO.: 3). Slight variants of each of these peptides would also be expected to retain activity for Streptococcus pyogenes.

Single amplification of a signal using a conventional gold conjugate and lateral flow is less sensitive than a two-conjugate system whereby an active enzyme, such as a protease, hydrolyzes the peptide target from the first conjugate (amplification 1) that leads to the binding of the second conjugate (amplification 2).

In one example, a two-chamber device consists of an enzyme reaction chamber that snaps into a lateral flow cassette that includes a conjugate pad and a lateral flow strip. Thus, in one embodiment, the enzyme reaction chamber is removable, and optionally, comprises a membrane. In one embodiment of the present invention, the membrane is a size-exclusion membrane. For example, the membrane can exclude particles of greater than about 1 micron. The membrane can comprise absorbent material, non-absorbent material, or a hollow tube or fiber. In another embodiment, the membrane filters unmodified substrate away from modified enzyme substrate, such that only modified substrate enters the conjugate pad. In another embodiment, the conjugate pad itself acts as a filter.

The enzyme-mediated reaction can take 5-15 minutes and, after a use-dependent or use-independent timed-release of the material, the sample flows from the enzyme reaction chamber into the conjugate pad of the lateral flow cassette. Optionally, the sample flows out of the enzyme reaction chamber through a membrane and into the conjugate pad of the lateral flow cassette.

In a dual affinity assay, a second conjugate (e.g., gold) can be collected, for example, using a filter, tangential flow, or lateral flow. The gold conjugate can be collected as a line or in a pattern represented by the "+" symbol. In one embodiment, collection of the gold conjugate is through a binding interaction between the dual affinity tag (biotin and polyhistidine) on the clipped peptide in the following manner: the polyhistidine on the clipped peptide binds to the gold conjugate, which is derivatized with nitrilotriacetic acid (NTA). As the gold flows through by transpiration, across by transpiration, or along a liquid path through the membrane, it is captured on the membrane through the interaction of the biotin with streptavidin, which is coated onto the membrane in a line or pattern.

In one embodiment, the device comprises a positive control area containing a second specific binding partner that binds to a second conjugate, wherein the presence of a signal in the positive control area indicates the device has operated properly. For example, a lateral flow strip can comprise the positive control area. As a "positive control," a secondary line or pattern can be printed with a polyhistidine peptide. The polyhistidine peptide binds to the NTA-labeled gold conjugate through an interaction between $Ni^{2+}$ ions bound to NTA, and a cluster of at least four polyhistidine residues.

In yet another aspect of the invention, the second conjugate is less than about 1 micron in diameter, such as about 1 to about 10 nm, about 1 to about 50 nm, or less than about 1 nm. The second conjugate of the present invention can comprise at least one affinity label or at least two different affinity labels, for example NTA and biotin.

The conjugate pad of a lateral flow cassette can include a second conjugate. In another embodiment, a membrane of the enzyme reaction chamber can include a second conjugate.

The devices of the present invention can be used in any situation where it is desirable to detect the presence or absence of bacteria and, in particular, *Streptococcus pyogenes*. For example, bacteria that collects on work surfaces in health care facilities, and in particular in operating rooms, can be detected with a biosensor as described herein. A substrate, or more than one substrate, that can be modified by an enzyme produced and/or secreted by (e.g., presented on the surface of) a bacterium is labeled and covalently bound to a collector substrate, such as cotton fibers on the tip of a swab. When more than one substrate is utilized, each may be labeled so as to distinguish it from another (for example, using different detectable labels) and/or each may be localized in a particular region on the solid support. The swab tip is used to wipe the surface suspected of being contaminated by bacteria. The swab tip is placed in medium and incubated using conditions that allow modification of the labeled substrate if an enzyme (e.g., a protease) specific for the bound, labeled substrate(s) is present.

The present invention also features a biosensor for detecting a (one or more, for example, at least 2, at least 5, at least 10, at least 20, at least 30, at least 50, at least 75, or at least 100) marker protein enzyme(s) described herein and for notifying a consumer of the presence of the marker protein. As used herein, a "biosensor" is a device that incorporates one or more of the above-described substrates, or other substrates described herein, and produces a detectable signal upon sensing the presence or absence of bacteria. In one embodiment, a biosensor for use in healthcare settings or home use to detect strep throat comprising a (one or more) specific substrate(s) that is coupled to a solid support that is proximal to a fluid sample that is being monitored for bacterial contamination is provided. The substrate is covalently bound to a label and thus has a detection signal that, upon proteolysis of the substrate-label bond, indicates the presence of the bacteria. The biosensor of the present invention can be any medical device or consumer product, including, but not limited to, lateral flow assays, chest drains, catheters (such as those used for urinary tract infections), toothbrushes, or wound dressings. In one embodiment, the biosensor is a lateral flow device.

Because the methods and devices of the present invention are so sensitive, the sample need not be obtained from the back of the throat when detecting strep throat. The sample can be obtained from the inside of the cheek (e.g., between cheek and lower gums) or on the tongue using an appropriate solid support (e.g., toothbrush, swab).

The biosensor is made by first determining the specific substrate of a specific enzyme characteristic of the bacteria to be detected. The determined specific substrate is labeled with one or more, and preferably, a plurality of detectable labels, for example, chromatogenic or fluorescent leaving groups. Most preferably, the labeling group provides a latent signal that is activated only when the signal is proteolytically detached from the substrate. Chromatogenic leaving groups include, for example, para-nitroanalide groups. Should the substrate come into contact with an enzyme secreted into a wound or other body fluid by bacteria or presented on the surface of a bacterial cell, the enzyme modifies the substrates in a manner that results in detection of such a modification, for example, a change in absorbance, which can be detected visually as a change in color (for example, on the solid support), or using spectrophotometric techniques standard in the art.

The biosensor of the present invention can also comprise one or more substrates (for example, at least 2, at least 5, at least 10, at least 20, at least 30, at least 50, at least 75, or at least 100 substrates) for produced and/or secreted enzymes of pathogenic bacteria. The biosensor can further include a solid support, for example, a wound dressing (such as a bandage, or gauze), a toothbrush, any material that needs to be sterile or free of microbial contamination, for example, a polymer, disk, scope, filter, lens, foam, cloth, paper, dipstick, chest drain, sutures, or an article that contains or collects the sample (such as a urine collection bag, blood or plasma collection bag, test tube, catheter, swab, or well of a microplate).

Typically, the solid support is made from materials suitable for sterilization if the support directly contacts the sample. In one embodiment of the present invention, the biosensor can be directly contacted with the wound. In some instances, a sterile covering or layer is used to prevent contamination of the wound or body fluid upon such direct contact. If such sterile coverings are used, they will have properties that make them suitable for sterilization, yet do not interfere with the enzyme/substrate interaction. Preferably, the portion of the biosensor that comes into contact with the wound is also nonadherent to permit easy removal of the biosensor from the sample surface. For example, if the biosensor comprises a wound dressing, the dressing contacts the wound for a time sufficient for the enzyme substrate to react and then the dressing is removed from the wound without causing further damage to the wound or surrounding tissue. The solid support of the biosensor can also be beads (e.g., Trisacryl or Hyper D).

In one embodiment of the invention, detection of *Streptococcus pyogenes* activity can be measured with peptide-conjugated beads in a number of formats including, but not limited to, fluorescence resonance energy transfer (FRET), microplate assays, colorimetric assays (e.g., Azo casein), lateral flow, filtration, or tangential flow filtration. The beads can be functionalized beads (e.g., Trisacryl or Hyper D).

In fluorescence resonance energy transfer (FRET) as described by U.S. Pat. No. 6,908,769 (the contents of which are incorporated herein in their entirety), there is a spatially-dependent quenching of a fluorescent molecule with a quenching molecule. For example, a peptide of SEQ. ID. NO.: 1, 2, or 3 is placed between a DABCYL quenching group and a Fluorescent EDANS group and, because the peptide is small, the DABCYL dye quenches the EDANS fluorophore. Because the fluorescent dye is within 100 angstroms of the quenching dye, it is quenched until the peptide is hydrolyzed.

In another embodiment of the present invention, a dye-labeled peptide can be released when the peptide comprising the amino acid sequence of SEQ. ID, NO.: 1, 2, or 3 is hydrolyzed and the dye can be detected, for example, spectrophotometrically or by visual inspection.

In another embodiment of the present invention, the substrate is a dual affinity-labeled peptide (example of affinity labels include, but are not limited to, biotin and polyhistidine). Upon cleavage of the peptide from a tether such as a bead, the released peptide can subsequently bind to a conjugate, for example a NTA-functionalized gold conjugate, in a microplate then be measured through the binding of a secondary analyte, for example NTA-horseradish peroxidase. The analyte need not be antibody-based, as described in other lateral flow immunochromatographic devices. Instead, the analyte may rely on other specific binding interactions, such as that of nitriloacetic acid (NTA) to polyhistidine through a nickel affinity interaction or through the very stringent and specific binding of streptavidin (or neutravidin) to biotin, carboxybiotin, or other biotin derivatives or analogs. In one particular microplate format, the clipped peptide tagged with a dual affinity tag (e.g., biotin and polyhistidine) is first bound to a streptavidin-coated microtiter plate and, after a series of washes and blocking with detergent or protein, the reaction is detected using NTA-labeled horseradish peroxidase (HRP) and by incubating with a colored substrate such as 3,3',5,5'-tetramethylbenzidine (TMB), 2,2'-azino-bis(3-ethylbenzthiazoline-6-sulphonic acid) (ABTS) or other suitable fluorescent or colorimetric substrates.

In the case of (1) lateral flow, (2) tangential flow or (3) filtration, the clipped dual affinity tag can bind to a NTA-labeled gold particle and, because of its small size, the gold particle easily filters through a membrane or hollow fiber material to collect onto the surface. The binding can be made more specific by printing a second specific binding partner (e.g., streptavidin) onto the surface of the membrane. As used herein, "first conjugate" (e.g., peptide-labeled beads) refers to an enzyme substrate that is modified by an enzyme produced and/or secreted by a bacterium and releases a signal in the form of a modified first conjugate (e.g., an affinity-labeled peptide). This can be, e.g., a first amplification and the first conjugate can be a first amplifier. As used herein, "second conjugate" refers to a partner in a specific binding interaction, for example with a first conjugate, a modified first conjugate, or a second specific binding partner, that flows with the solution and amplifies the signal released by the first conjugate. This can be, e.g., a second amplification, and the second analyte can be a second amplifier. In one embodiment, the second conjugate comprises gold or latex particles. The second conjugate can be labeled with an affinity tag (e.g., Ni-NTA). In a preferred embodiment, the second conjugate is about 1 to about 50 nm in diameter, or about 1 to about 10 nm in diameter, or less than about 1 nm in diameter. In other embodiments, the second conjugate can comprise or consist of an affinity tag and a color-producing label.

As used herein, "second specific binding partner" refers to a partner in a specific binding interaction, typically with a first conjugate, modified first conjugate or second conjugate, that is, for example, immobilized onto a membrane (e.g., streptavidin, antibody, polyhistidine). In some embodiments, the affinity partner is covalently bound to the membrane. In other embodiments, the affinity partner is dried on to the membrane (e.g., nitrocellulose).

The membrane can be made of material that is absorbent or non-absorbent, opaque or transparent, charged or neutral, and can further be modified by spraying with adhesive or attached to another surface using RF welding. In some embodiments of the invention, the membrane can be made of nitrocellulose or polyether sulfone. In some embodiments, the membrane can be a size-exclusion membrane. In some embodiments, when cross-flow is preferred, non-absorbent material may be used. In other embodiments, where lateral flow is preferred, an absorbent material may be used. In some embodiments, where tangential flow is preferred, a hollow fiber may be used.

In another embodiment, the second conjugate carrying the released substrate is able to be filtered through a size exclusion membrane and collect on the surface. In some embodiments, collection on the surface is passive, due to transpiration, or active, due to a positively or negatively charged surface or a second specific binding partner. In other embodiments, the dimensions of the flow path area is modified, either by charge or the binding of a second affinity tag and can result in the formation of a pattern such as a circle, cross, or a line on the membrane. In yet other embodiments, the size-exclusion membrane is non-absorbent material for cross-flow purposes. In still yet other embodiments, the size-exclusion membrane is an absorbent material for the purpose of lateral flow. In other embodiments, the size-exclusion membrane is a hollow fiber for the purpose of a tangential flow path.

Optionally, in a lateral flow device, a "positive control" line, made, for example, of polyhistidine or streptavidin, can be printed on the flow strip with, e.g., a Biodot printer, and then dried (e.g., at 40° C.) for at least one hour prior to incubating with a gold conjugate. In one example, the control line can be 0.5 mg/mL poly-L-histidine in water. When the strips are run, the control line remains dry for several seconds before it begins to fill in with the buffer and the signal forms by binding of, for example, a second conjugate, such as Ni-NTA-functionalized gold particles.

The signal can be in any detectable form. Patterns other than a line are also possible as signals on the flow strip. As used herein, "pattern" refers to the demarcations located on the flow strip that signal a positive or negative assay. In one embodiment, the patterns are in the form of shapes, such as a line, a circle, or a cross. In one embodiment, the signal on the lateral flow strip can comprise a pattern.

In yet another embodiment of the present invention, a detectable signal on a membrane indicates the presence of a bacterium and/or protease present in a sample. The signal can be produced by the second conjugate collecting on the surface of a membrane. The membrane comprises nonabsorbent material or absorbent material, or can be a hollow fiber. The second conjugate can collect on a second membrane after filtration through a size-exclusion membrane. The second conjugate can collect on the surface of a membrane by transpiration or can actively collect due to a negatively or positively charged surface. The second conjugate can collect as the result of a binding interaction with a second specific binding partner (e.g., avidin or polyhistidine). The collection on the surface can lead to a pattern (e.g., circle, line, cross).

In some examples, *Streptococcus pyogenes* can be detected either by growing it in a protein-rich medium such as sterile THY media (Todd Hewitt media, supplemented with 2% yeast extract) or with clinical samples in which the patient has presented with a sore throat and/or is positive by an antibody-based test which has high specificity. One benefit of a protease assay for step throat is that there is a much higher sensitivity than the current antibody-based professional care tests. Cultures that are negative by an antibody-based test are not necessarily a true negative due to the poor sensitivity of antibody-based tests. Since a protease-based test has a two-fold amplification as compared to a simple antibody-based test, the sensitivity is much greater (about 10 to about 100 times greater, for example).

The present invention also features a kit for detecting bacteria (e.g., *Streptococcus*) as described herein. The kit can comprise a solid support, for example, having a plurality of wells (e.g., a microtiter plate), to which a detectably labeled substrate is linked, coupled, or attached. A means for providing one or more buffer solutions is provided. A negative control and/or a positive control can also be provided. Suitable controls can easily be derived by one of skill in the art. A sample suspected of containing a pathogen described herein can be prepared using buffer solution(s). Aliquots of the sample, negative control, and positive control can each be placed in its own well and allowed to react. Those wells where modification of the substrate, for example, a color change is observed are determined to contain a microbial pathogen. Such a kit is particularly useful for detecting strep throat in a subject.

The term "subject," as used herein, refers to a mammal. In one embodiment, a subject is a human or other animal patient.

Also encompassed by the present invention is a kit that comprises a bio sensor, such as a packaged sterilized wound dressing, and any additional reagents necessary to perform the detection assay.

The methods and/or devices of the present invention can be used to detect the presence or absence of any strep throat-specific enzyme described herein. For example, the method and/or biosensors can be used to detect the presence or absence of protease enzymes secreted by *Streptococcus*, such as *S. pyogenes*. In another embodiment, the methods of devices of the present invention can be used to detect anaerobic organisms. In another example, it has been discovered that certain bacteria secrete lipases into their environment as part of their survival and/or virulence mechanisms. The lipases serve to break down lipids in the growth environment in order to release nutrients. Lipases may also play a role in disarming mammalian host defenses during infection. Synthetic substrates for these secreted enzymes can be employed to detect the presence of those pathogenic bacteria that secrete them. By synthesizing lipids attached to dye moieties, it is possible to create substrates that will change color as they are hydrolyzed by secreted lipases. The dye molecule can be one of many commercially available molecules that are colorless when attached to fatty acids, and change color when the substrate is cleaved by lipase. An example of such a dye is Rhodamine-110 (available from Molecular probes, Eugene, Oreg.). This color change forms the basis of a bacterial sensor, which can be incorporated into healthcare products including, but not limited to, wound dressings.

A method for developing an assay for detecting a pathogenic bacterium that produces at least one enzyme that is secreted by the cell or present on the surface of the cell (e.g., *S. pyogenes*) and a method for using the assay to detect the pathogenic bacterium producing the enzyme(s) now follows:

Step 1) Define an amino acid sequence that uniquely identifies the prokaryotic microorganism of interest. Alternatively an amino acid sequence that is unique to a specific group of pathogens, for example, wound-specific pathogens can be determined.

Select an amino acid sequence, for example, a protein, peptide, or polypeptide (marker sequence) that uniquely characterizes or marks the presence of the microorganism or group of microorganisms (for example, wound-specific pathogens) of interest. The selection can be performed utilizing a bioinformatic approach, for example, as described in detail below. One or more amino acid sequences that are unique to a specific prokaryotic microorganism are determined.

Step 2) Obtain sufficient enzyme to determine conditions facilitating optimal modification of a substrate by the enzyme.

Isolate the enzyme from the extracellular medium in which the pathogenic bacteria to be assayed is growing, or from the cell membrane of the bacteria, using standard protein purification techniques, described, for example, in Ausubel (supra).

Alternatively, if the genetic sequence encoding the enzyme or the location of the genetic sequence encoding the enzyme are unknown, isolate and clone the genetic sequence encoding the marker amino acid of Step 1, or, first determine the genetic sequence, and then proceed as before.

Step 3) Determine the conditions for growth of the prokaryotic organism and for the production of an enzyme presented on the surface of the cell or secreted by the cell.

Determine medium required for growth of the specific prokaryotic microorganism of interest and for expression of its unique active enzyme into the medium. Also determine whether a second molecule, for example, an enzyme is required to convert the specific enzyme from an inactive precursor form to an active form. To determine if the enzyme has been secreted in an active form, a sample of the bacterial culture is provided with chosen potential substrates and cleavage of these substrates is determined. This can be done, for example, by combining the bacteria that produce the enzyme with the substrate in the appropriate media and incubating at 37° C. with gentle shaking. At preset times (0.1, 0.3, 1.0, 3.0, 5.0, 24 and 48 hours) the samples are centrifuged to spin down the bacteria, and a small aliquot is removed for an SDS-PAGE gel sample. After completion of the time course, the samples are run on a 10-15% gradient SDS-PAGE minigel. Then, the proteins are transferred to Immobilon Pseq (Transfer buffer, 10% CAPS, 10% methanol pH 11.0, 15 V for 30 minutes) using a Bio-Rad semi-dry transblotting apparatus. Following transfer of the proteins, the blot is stained with Coomassie blue R-250 (0.25% Coomassie Brilliant Blue R-250, 50% methanol, 10% acetic acid) and destained (high destain for 5 minutes, 50% methanol, 10% acetic acid; low destain until complete, 10% methanol, 10% acetic acid) followed by sequencing from the N-terminus. Alternatively, the samples can be run on a mass spectrometer in order to map the sites of proteolytic cleavage using, for example, a Voyager Elite Mass spectrometer (Perceptive Biosystems, Albertville, Minn.).

Step 4) Identify any specific substrate(s) of the active enzyme protease. Examples of potential substrates include proteins, peptides, polypeptides, lipids, and peptidoglycan subunits. Label each substrate with a detectable label, for example, a detectable label described herein, or any other detectable label known in the art.

Step 5) Increase the specificity of the enzyme-substrate interaction (optional) by determining the active or binding site of the enzyme (for example, using FRET as described above), then determining the genetic sequence useful for producing the active or binding site, and cloning the determined genetic sequence to generate a more specific substrate.

Step 6) Provide a biosensor comprising one or more of the detectably labeled substrates identified above for detection of the protease of the pathogenic bacteria of interest.

The substrate can be attached to solid support, for example, a wound dressing, or an article that holds the enzyme and substrate, for example, a body fluid collection tube or bag, a microplate well, a test tube, or any solid support described herein. The solid support, if desired, can provide a plurality of derivatized binding sites for coupling to the substrate, for example, succimidyl ester labeled primary amine sites on derivatized plates (Xenobind plates, Xenopore Corp., Hawthorne, N.J.).

Optionally, unoccupied reactive sites on the solid support are blocked by coupling bovine serum albumin, or the active domain of p26 thereto. p26 is an alpha-crystallin-type protein that is used in this case to reduce non-specific protein aggregation. The ability of the p26 protein to refold heat denatured citrate synthetase before and after coupling to the surface of the food packaging is used as a control for determining p26 activity. Alpha-crystallin-type proteins were recombinantly produced using standard recombinant DNA technologies (see Ausubel, supra). Briefly, the plasmid containing the beta sheet-charged core domain of p26 is electroporated into electrocompetent BL21(DE3) cells (Bio-Rad E. coli pulser). The cells are grown up to an $OD_{600}$ of 0.8, then induced with 1 mM IPTG for 4 hours. The cells are spun down, and sonicated in low buffer (10 mM Tris, pH 8.0, 500 mM NaCl, 50 mM Imidizole) to lyse (Virsonic, Virtis, Gardiner, N.Y.). The lysate is spun down at 13,000×g for 10 minutes, and the supernatant 0.45 and 0.2 Φm filtered. This filtrate is loaded onto a Ni-NTA superose column (Qiagen, Valencia, Calif., cat #30410). High buffer (10 mM Tris pH 8.0, 500 mM NaCl, 250 mM imidazole) is used to elute the protein.

Allow the enzyme(s) to come into contact with the substrate(s), and monitor the reaction for a modification in the detectably labeled substrate, as described herein. Modification of the substrate indicates that the enzyme produced/secreted by the bacteria is present in the reaction. In addition, the absence of modification of the substrate indicates that the enzyme is not present in the sample.

EXEMPLIFICATION

The present invention will now be illustrated by the following Examples, which are not intended to be limiting in any way.

Example 1

Detection of Streptococcus pyogenes

The hydrolysis of a Streptococcus pyogenes-specific peptide FLVMFLSG (SEQ. ID. NO.: 1) from Tris Acryl or Hyper D beads was used to detect Streptococcus pyogenes in samples. The signal of this peptide hydrolysis reaction was reamplified by binding of the released substrate to a gold conjugate (or NTA-HRP) and measured by lateral flow technology or microplate assay. Use of the peptide of SEQ. ID. NO.: 1 in a microplate assay (EXPRESS DETECT®, ECI, Worcester, Mass.) resulted in detection of S. pyogenes at levels lower than those detected by the broad spectrum peptide, CPI2 (see WO2005/0427700, the contents of which are incorporated herein in their entirety).

FIG. 1 is a plot of S. pyogenes concentration (CFU/mL) versus the rate of color development (mOD/min) and illustrates the detection of S. pyogenes in a sample by measuring the color development that results when the S. pyogenes-specific peptide, H11 (SEQ. ID. NO.: 1), is hydrolyzed from beads and amplified using NTA-HRP. Specifically, cell-free medium from S. pyogenes cultures grown to $10^7$ CFU/mL was diluted to the equivalent of $10^5$ or $10^3$ CFU/mL, and 100 µl was assayed for proteolytic activity toward the peptide of SEQ. ID. NO.: 1. The assay effectively detected S. pyogenes at $10^3$ CFU/mL.

Example 2

Example of a Lateral Flow Device

A detectable label comprising a dual affinity tag (biotin and polyhistidine) is covalently linked to the C-terminus of a peptide substrate, which in turn IS linked to the surface of a bead. The detectable label, the peptide substrate, and the bead, together, make up the first conjugate. Microbial proteases present in *Streptococcus* cleave a multiplicity of first conjugate peptide substrates, releasing free detectable label from the bead. After release by proteases, the free detectable label (also referred to herein as modified first conjugate) is separated from the beads and unmodified first conjugate by filtration through a lateral flow membrane device.

A solution containing the released detectable label is applied directly to a lateral flow strip or a conjugate pad in fluid communication with the lateral flow strip. The lateral flow strip has a first region containing an excess of second conjugate, for instance, nanometer-sized gold nanoparticles labeled with Ni-NTA-bovine serum albumin (BSA). A second region of the lateral flow strip contains a second specific binding partner, for instance, streptavidin in the case of a biotin affinity tag, bound to the lateral flow membrane. A third region contains a reagent bound to the membrane that serves as a positive control (to demonstrate that the device has functioned properly). The positive control reagent can be, for example, a second specific binding partner that binds to a second conjugate.

Liquid flow in the membrane is driven by the wicking pad. A multiplicity of detectable labels flow with the liquid within the membrane into the first region where the second conjugate (e.g., Ni-NTA-BSA-labeled gold nanoparticles), if present, interacts with and binds one portion of the dual affinity tag (e.g., histidine) of the detectable labels to form a multiplicity of soluble complexes (a first amplification). The soluble complexes continue to flow with the liquid within the membrane toward the wicking pad so that the soluble complexes enter the second region.

The multiplicity of membrane-bound second affinity binding partners (e.g., streptavidin) within the second region interacts with and binds to the second affinity tag (e.g., biotin) of the detectable labels or soluble complexes and prevents them from flowing down the membrane. This interaction causes a multiplicity of soluble complexes to accumulate within this region, generating a visible color change when sufficient quantity has accumulated (a second amplification).

Figure 3:
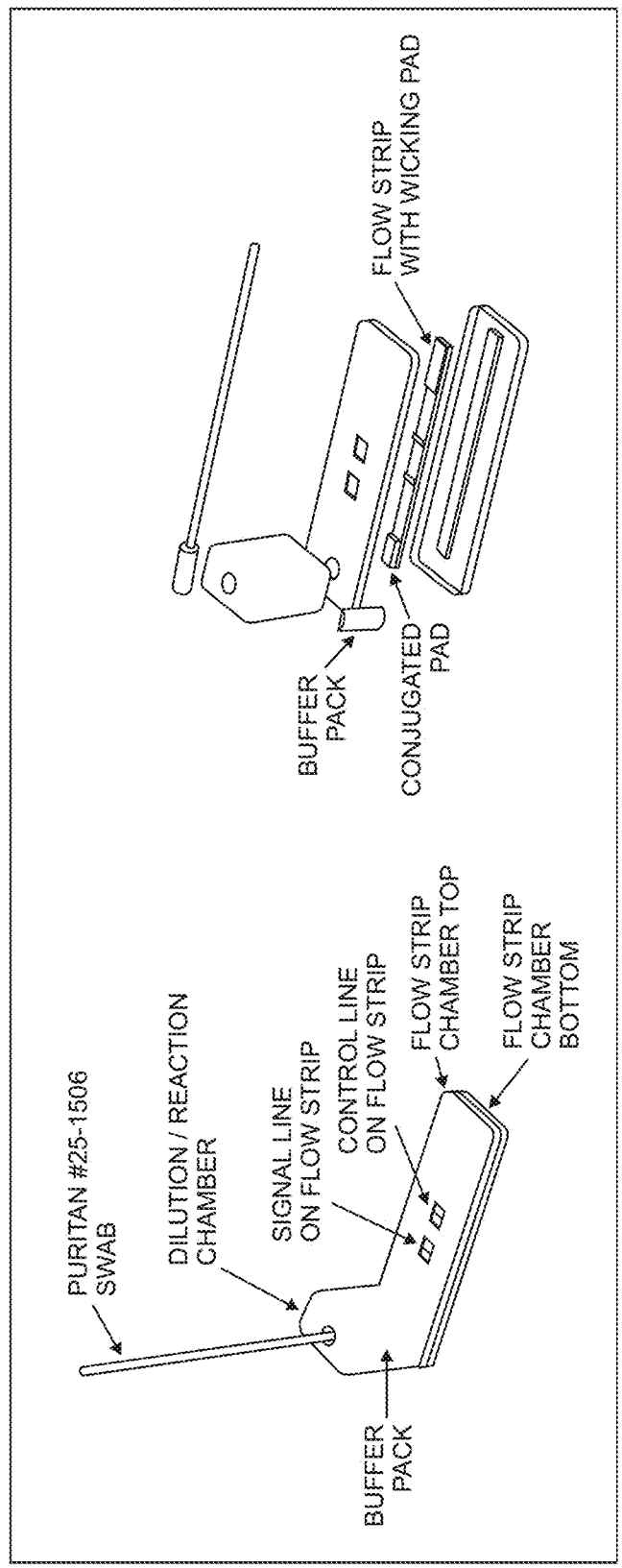
FIG. 3 is a diagram of one embodiment of a lateral flow device of the present invention.
Figure 8:
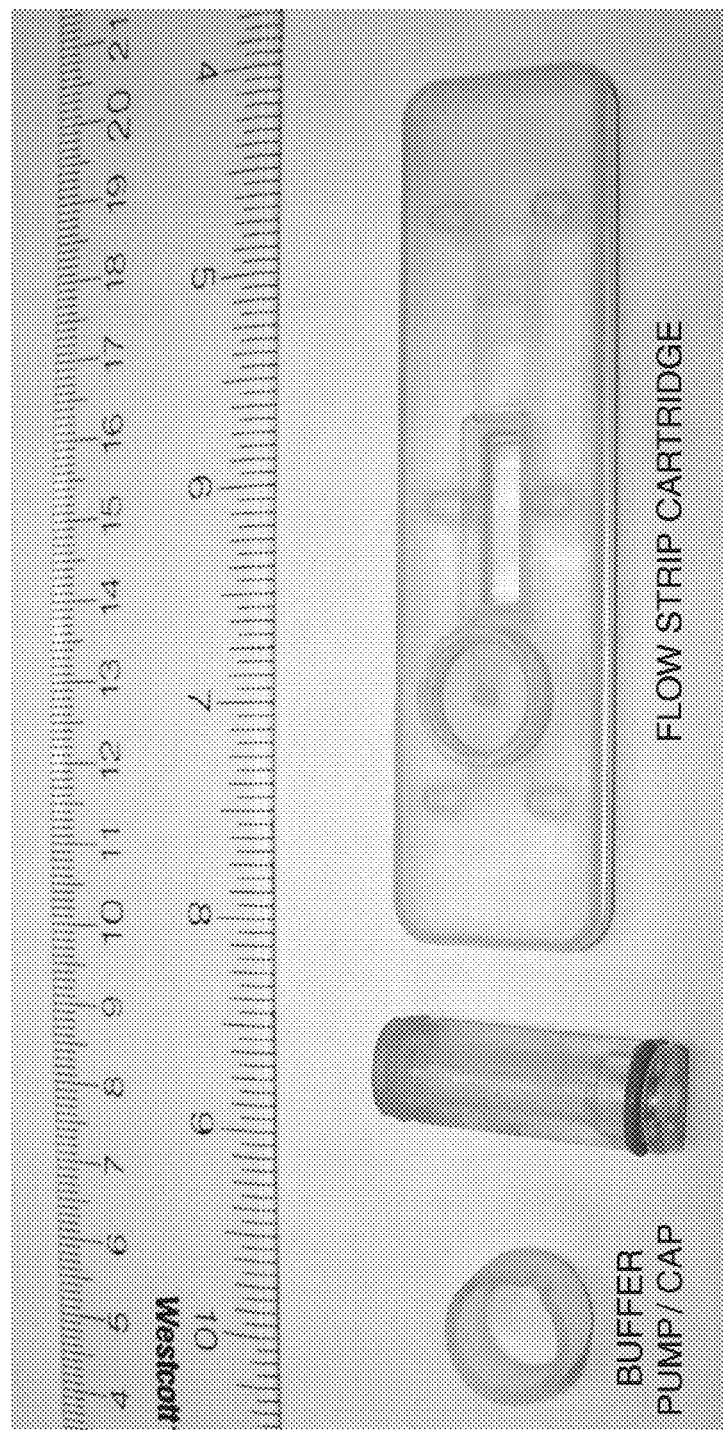
FIG. 8 is a diagram of one embodiment of a lateral flow device of the present invention comprising an enzyme reaction chamber that snaps into a lateral flow cassette.

If there is absence of free detectable label applied to the membrane, there will be no interaction with the multiplicity of second conjugates or second specific binding partners, and no production of color within the signal/test region. The soluble second conjugate that is not bound by free detectable label continues to flow with the liquid within the membrane until it reaches a third region where the second conjugate interacts with and binds a multiplicity of membrane-bound reagents (e.g., Ni-NTA) so that sufficient second conjugate accumulates to generate a color change within this third region. As this binding event, and its associated color generation, are independent of the presence of free detectable label, the color within this region serves as a positive control to demonstrate that the lateral flow device has operated properly. See FIGS. 3 and 8 for sample devices.

In some embodiments, the conjugate pad serves the purpose of the membrane in the reaction chamber, preventing the first conjugate, but not the modified first conjugate or the second conjugate, from entering the lateral flow strip. In these instances, the reaction chamber need not comprise a separate membrane.

Example 3

Microplate Assay for Analysis of *Streptococcus* Samples

Figure 2:
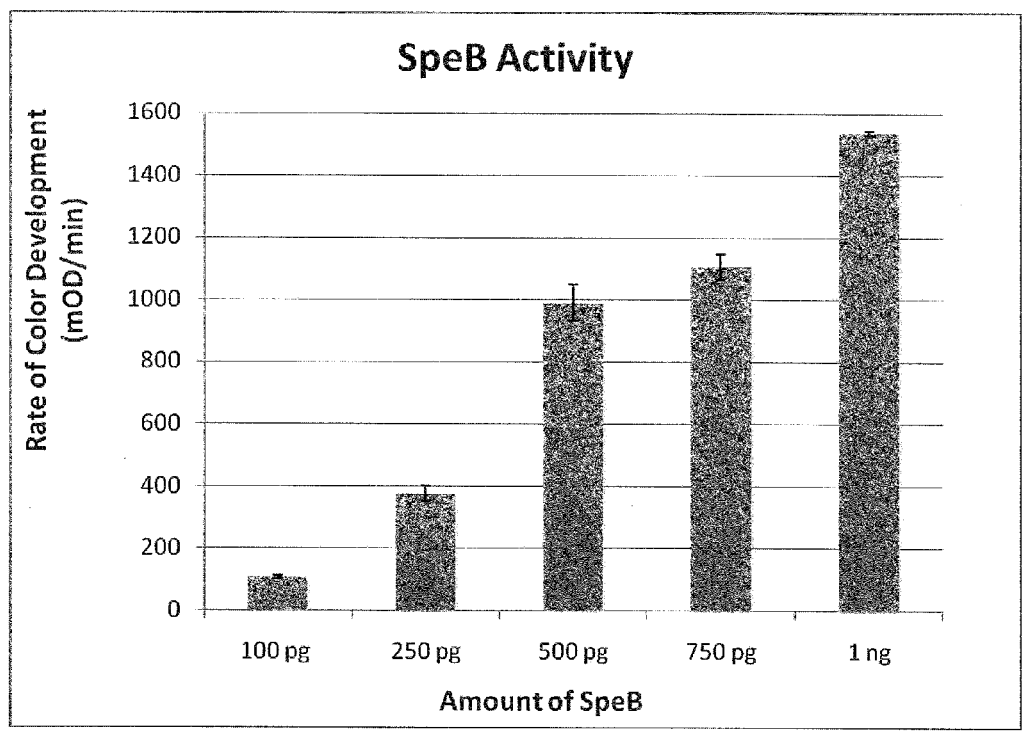
FIG. 2 is a plot of the amount of SpeB (ng or pg) versus the rate of color development (mOD/min).

FIG. 2 is a plot of the amount of streptococcal pyogenix exotoxin B (SpeB) (ng or pg) versus the rate of color development (mOD/min) and illustrates the detection of SpeB in a sample by measuring the color development that results when H11 peptide is hydrolyzed from beads and amplified using NTA-HRP. SpeB was purified from *S. pyogenes* growth media according to Kapur et al. PNAS: 1993, vol. 90, no. 16, pages 7676-7680 (with minor modifications). Cell-free growth media from *S. pyogenes* was desalted on a G25 Sephadex column, then SpeB was purified by affinity chromatography using a Reactive Red-120 agarose column. Purified SpeB was diluted to 1-10 ng/mL in 50 mM Tris buffer, pH 8.0, and a 100-μl aliquot was tested for proteolytic activity in a microplate assay (ECI, Worcester, Mass.) with the peptide of SEQ. ID. NO.: 1. The lower limit of detection was 100 pg of purified SpeB. A detailed procedure is outlined below:

Clinical Sample Preparation

1. The swab samples will be frozen at −20° C. immediately after collection at the clinical site, transported to ECI in Styrofoam containers containing wet ice, and maintained at −20° C. until analysis (unless otherwise specified in the specific experimental protocol).
2. Perform swab extraction while working in a laminar flow hood.
3. Thaw the swabs on ice just prior to analysis.
4. Extract each swab (small) in 350 μL of 50 mM Tris buffer, pH 8.0, by inserting the swab into a 15-mL conical tube containing Tris buffer. Absorb as much of the buffer as possible into the swab by twisting for 15 seconds. Large swabs should be extracted in the same manner in 500 μl buffer.
5. Extract the fluid from the swab by pressing the swab against the wall of the tube.
6. Use a p1000 pipette to remove any additional liquid remaining in the swab and combine this with the liquid in the original extraction tube.
7. Keep swab extract on ice throughout the microplate experiment.

Standard SpeB and *S. Pyogenes* Supernatant Preparation

1. Standard SpeB and supernatant preparation can take place outside of the laminar flow hood.
2. For standard curve, or if analyzing only purified SpeB and not clinical samples, thaw an aliquot of SpeB on ice and note the lot number and concentration.
3. Prepare standard dilutions of SpeB according to directions above or prepare dilutions in 7% saliva in 50 mM Tris, pH 8.0, necessary for the amount of SpeB being studied that allows for addition of buffer to a final volume of 100 μl.
4. If measuring activity of *S. pyogenes* supernatant, note the CFU/mL of the stock supernatant and dilute to the desired concentration in the 7% saliva solution.

Sample Analysis

1. Fill out a 96-well template to indicate what samples are in each well.
2. Negative control samples containing fill-conjugated beads with 7% saliva in Tris buffer alone and standard curve samples containing purified SpeB in matrix blank must be included.
3. Sixty microliters of beads at a concentration of 180 mg/mL are required for each well. Calculate the volume of beads needed for the experiment by multiplying the number of wells used by 60.
4. If using wet H11 beads stored in 3 ppm Proclin at 4° C., remove a 1-mL aliquot of beads; place the aliquot in a 2-mL microcentrifuge tube and centrifuge for 30 seconds at 5,000 rpm using a bench-top centrifuge. Remove the liquid from the top of the beads using a pipette.
5. Tare the analytical balance, place an empty 2-mL microcentrifuge tube on the pan and tare again. Remove the empty tube and place the tube containing the bead aliquot on the pan to measure the mass of the beads.
6. Wash the H11-bead aliquot five times with 1 mL PBS followed by washing five times in 50 mM Tris buffer, pH 8.0, using centrifugation for 30 seconds at 5,000 rpm using a bench-top centrifuge. Remove buffer with a pipette in between washes.
7. Re-suspend the beads in 50 mM Tris, pH 8.0, at a concentration of 180 mg/mL using the mass measured in Step 5. For aliquots of beads greater than 180 mg, bring the beads up to a final volume of 1 mL (taking into account volume of the beads themselves) and then add the remaining volume.
8. Based on the volume calculated in Step 3, if more beads are required for the experiment, repeat Steps 4-7 with a new aliquot.
9. Combine multiple washed aliquots into 1 tube (if applicable) and pipette up and down to mix thoroughly.
10. Resuspend the bead aliquot by pipetting up and down with a p200 pipetman equipped with a large orifice tip. Using large orifice pipette tips, add 60 μl H11-bead conjugate to each of the wells of a 96-well filter plate.
11. If using dried beads, resuspend each bead aliquot in 1 mL of 50 mM Tris, pH 8.0. This results in a concentration of 180 mg/mL and is enough for 16 wells at 60 μl/well. If additional beads are needed, resuspend additional aliquots. Using large orifice pipette tips, add 60 μl H11-bead conjugate to each of the wells of a 96-well filter plate according to the 96-well template.
12. Add sample extract, positive control protease standard, or 7% saliva in Tris buffer negative control to the wells. If needed, adjust the volume of sample to 100 μl by adding additional 7% saliva buffer to the sample wells.
13. Determine the number of streptavidin-coated 8-well strips needed and place them in a frame according to the layout of the filter plate.
14. Place the frame containing streptavidin wells below the filter plate containing samples and incubate for 30 minutes at room temperature while shaking.
15. If there are washed beads remaining, centrifuge the beads for 30 seconds using a bench-top centrifuge and remove the supernatant buffer.
16. Resuspend the beads in 1 mL of 3 ppm Proclin and transfer them back to the stock tube. Beads can be stored at 4° C. and washed to use in subsequent assays for 2-3 weeks.
17. If dried beads were used, discard any remaining beads.
18. After the 30-minute incubation, centrifuge the filter plate with streptavidin wells below it for 30 seconds, using FIBERFuge 3 k plus centrifuge (centrifuge has only 1 speed) so that the filtrate is collected in the streptavidin-coated wells.
19. Incubate the filtrate in the streptavidin plate for 1 hour at room temperature with shaking.
20. Invert the wells over a dish to empty filtrate from the wells and blot the wells on paper towel to remove residue. Using a multichannel pipette, add 250 μl of TBS-T to the wells and incubate for 5 minutes at room temperature while shaking. Invert the wells to remove the buffer, blot on a paper towel, and repeat the 5-minute wash two additional times for a total of 3 rinses.
21. Remove the buffer and add 100 μL of NTA-labeled-HRP diluted 1:1000 in TBS-T for 1 hour at room temperature while shaking.
22. As soon as the 1 hour incubation starts, take the Sureblue TMB peroxidase substrate out of the 4° C. refrigerator and keep on the bench top until use. Turn on the microplate reader in order for the bulb to warm up.
23. Discard the liquid and rinse the wells three times with TBS-T for 5 minutes each at room temperature with shaking.
24. While waiting for the final, 5-minute wash, using the template tab, label the wells with sample designations, and set the plate reader to read at 650 nm for 5 minutes using the kinetic setting with the minimum interval between readings, and 5 seconds of shaking before each read.
25. Click on the Template tab to assign the wells to groups for analysis. The standard SpeB samples can be labeled as a standard curve group while the experimental samples can be labeled as unknowns. Within each group, wells that are a triplicate are labeled with the same name. Example: Groups=Standards, 3 wells of sample 0 pg, 3 wells of sample 100 pg, etc.
26. Remove the final wash from the plate by shaking out the liquid and blotting on a paper towel.
27. Pour out TMB substrate into a plastic pipette basin. Using a multichannel pipette, add 100 μL TMB substrate to each well, confirm that there are no bubbles present and immediately transfer the plate to the carriage of the plate reader.

Example 4

Example of a Lateral Flow Device Comprising Gold Particles

In one lateral flow format, the peptide is conjugated to carboxymethyl (CM) beads then dried onto the membrane of an enzyme reaction chamber, where buffer extracts sample material from a swab. Upon release of the proteases from the swab, the peptide of the first conjugate can be clipped from the CM beads and the second conjugate (1-10 nm gold) binds the modified first conjugate. Because the gold particles do not interfere or cross-react with the peptide-labeled CM beads, the small gold conjugate can be dried with the larger peptide labeled beads in the enzyme extraction chamber. Following hydration of a swab to release the sample components and re-suspension of the peptide-labeled beads, the small gold particles can co-exist with the peptide-labeled beads or can be dried directly into the conjugate pad, for example, as described by Charlton et al. in U.S. Pat. No. 6,485,982 (the contents of which are incorporated herein in their entirety). Briefly, a 0.5-μM nanogold stock solution (in 2 mM borate buffer, pH 7.0) is prepared and then diluted to a final concentration of 0.1 μM. The gold solution can be poured onto the conjugate pad, layered between plastic wrap or parafilm, and then dried in the oven at 40° C. for 2 hours. In other embodiments, the second conjugate is not dried onto the conjugate pad.

Example 5

**Purification of SpeB from Desalted *Streptococcus pyogenes* Cell-Free Growth Media by Means of Reactive Red 120 Dye Ligand Affinity Purification**

Phase 1: 50 mL Culture of *S. Pyogenes*

Day One:
1. Remove 200 µl from a frozen glycerol stock of *S. pyogenes* and dispense in a small puddle on a blood agar plate. Drag a sterile inoculating loop through the puddle and zigzag across the plate several times to isolate single colonies. Return stock to −80° C. Incubate the streaked plate agar side up overnight at 37° C.
2. Alternately, remove 100 µl from an overnight culture of *S. pyogenes* and dispense in a small puddle on a blood agar plate. Drag a sterile inoculating loop through the puddle and zigzag across the plate several times to isolate single colonies. Incubate the streaked plate agar side up overnight at 37° C.

Day Two:
1. Check that the colonies on the plate are surrounded by zones of beta-hemolysis (lightened and transparent, in comparison to the red coloration of the agar in areas far from the bacteria) as confirmation that the plate harbors *S. pyogenes*. Colonies themselves should be raised from the surface of the agar and transparent to white.
2. Colonies from plate can be used for inoculations on Day Two and up to one month later. Plate should be stored, sealed, at 4° C., agar side up.
3. Aliquot 10 mL THY media into a sterile 15-mL conical tube.
4. Transfer *S. pyogenes* colonies from the streaked plate to the THY media.
5. Cap the 15 mL conical tube tightly—*S. pyogenes* is an aerotolerant anaerobe. Cultures show better growth/increased SpeB activity by creating a semi-anaerobic environment. Incubate the THY liquid culture overnight at 37° C. with agitation at 250 rpm.

Day Three:
1. After incubating the liquid culture for 16-24 hours, check that it is turbid (indicating growth).
2. Aliquot 2.5 mL of the growing culture to each of 4×25 mL THY media in 50-mL sterile culture tubes.
3. Cap the four 50-mL conical tubes tightly and incubate the THY liquid cultures overnight at 37° C. with agitation at 250 rpm.

Day Four:
1. After incubating the liquid cultures for 16-24 hours, check that they are ready for harvest based on two criteria:
2. Cell count: From all four cultures, measure $A_{600}$ and use the conversion factor $OD_{600}=1::1.4\times10^7$ CFU/mL Cell density is expected to reach more than $10^7$ overnight so that it will be necessary to prepare dilutions of 1:10 and/or 1:100 and back-calculate in order to obtain accurate absorbance readings; and
3. Activity: From the four cultures, remove 500 µl cell suspension to a sterile MCT and spin for 1 minute at maximum speed in a microcentrifuge. Transfer the supernatant cell-free growth media to a new tube and discard the cell pellet. Use the supernatant in "Microtiter FRET assay for SpeB activity."
4. If cultures demonstrate typical activity and cell growth, $OD_{600}$ measurements should be made for the remaining cultures and then all can be harvested according to steps 3 and 4. Otherwise, leave to grow for an additional four hours and repeat steps a. and b. Only cultures demonstrating typical activity should be taken through the effort of SpeB purification.
5. Cap tubes tightly for removal from the Biosafety Level 2 area. Bring to the Beckman J-6 centrifuge and spin at 3000 rpm for 10 minutes at 4° C.
6. Combine 4×25 mL supernatants into two, labeled 50-mL conical tubes. Freeze at −80° C. until purification (up to one month). Discard the cell pellets.

Phase Two: Supernatant Desalting and Reactive Red 120 Dye Ligand Affinity Chromatography Prepare Spent Growth Media for Affinity Purification:
1. The 300 mL G25 Sephadex column is stored at room temperature in Buffer A. Before each use, equilibrate the G25 Sephadex column by running 1 column volume of Buffer A through at 5 mL/min and confirm that the UV absorbance is low and steady (varying by less than ±0.001 OD).
2. After thawing the CFGM, reserve 1 mL for later analyses at −20° C., and then load the remainder of the 100 mL to the G25 Sephadex column.
3. The Biologic Chromatography System is programmed to collect the G25 Sephadex column eluent in 10 mL fractions, once the 100 mL CFGM has finished loading onto the column, for the next 300 mL.
4. Once the 300 mL have eluted from the column, the 30×10 mL eluate fractions are evaluated for protease activity using the "Microtiter FRET assay for SpeB activity," with the CFGM Supernatant desalt loading fraction as a positive control.

Prepare Reactive Red agarose column: The Reactive Red-120 agarose column is stored between uses in a BioScale MT 10 column at 4° C., under Buffer A. Before use, wash it with 10 column volumes of Buffer A at room temperature, and confirm that UV absorbance is low and steady.

Red Agarose Affinity Purification:
1. Load the desalted CFGM, verified by Bradford Protein Concentration Assay, onto the RR-120 column at 3 mL/min. All flowthrough is collected in 10 mL fractions.
2. Wash the RR-120 column with 10 column volumes of Buffer A. If the UV absorbance is not low and stable after 10 column volume washes, add 5 more column volumes, and reassess. All washes are collected in 10 mL fractions.
3. Elute in 30 mL Buffer B. During the application of Buffer B to the column, an increase in both UV absorbance, indicating release of protein from the column, and an increase in conductivity, due to the higher salt concentration of Buffer B, should be observed. All eluent fractions from the RR-120 column are collected in 1 mL fractions.
4. Eluent fractions containing SpeB protein (based on high UV absorbance) will be verified initially by Bradford Protein Concentration Assay.
5. The three eluate fractions of highest concentrations, as assayed by the Bradford technique in Step 21, will be buffer exchanged in Phase 3.

Phase Three: Preparation of SpeB Protein for Storage by Gel Filtration Buffer Exchange:
1. The three eluate fractions of highest concentration will be combined. 50 µL from this combined lot will be removed to a separate 0.5 mL tube and frozen at −20° C. for later analysis.
2. 2.5 mL of the remaining pool will be loaded onto a PD-10 column, which has been equilibrated according to the manufacturer's directions. As the protein loads onto the column, buffer will drain from the bottom of the column; discard this buffer.
3. To exchange the buffer of the protein, position a clean, fresh 5-mL MCT tube below the PD-10 column to collect elution. Add 3.5 mL fresh PBS onto the PD-10 column. The protein will be in the 3.5 mL of liquid that elutes from the PD-10 as a result.
4. Once a volume of 3.5 mL has eluted from the PD-10 column, cap the 5 mL tube. Invert the tube gently several times to ensure a homogenous mixture.
5. If necessary, prepare tubes that will hold aliquots of the purified SpeB protein and use a repeat pipettor to aliquot the purified protein into the tubes. Store at intended conditions.

Example 6

Fluorescence Resonance Energy Transfer Peptide Microplate Assay for Analysis of Group A *Streptococcus* Samples 1. Fill out a 96-well template, indicating both which samples and which substrates are in each well.
2. In the top line of each well, indicate the sample (i.e., the substance whose protease activity is to be measured) to be placed in that well. If the well is a control, or "no sample" well, fill in the substance that will be substituted for sample (usually buffer).
3. In the second line, indicate the peptide substrate to be placed in the well. If the well is a control, or "no peptide" well, fill in the substance which will be substituted for peptide—usually the buffer used to dilute peptide with for the assay.
4. Include wells that will hold the EDANS standard curve. These wells are included in the plate map template. Plan to aliquot 100 μL of an EDANS curve standard to each well, plus 100 μL of diluted peptide substrate. Perform the EDANS curve.
5. Leave diluted peptide substrate on ice until required for use in the assay. Return 5 mg/mL concentrated stock peptide solutions to −80° C. storage.
6. Aliquot 100 μL of each sample or "no sample" control to appropriate wells in the FRET microassay plate.
7. Aliquot 100 μL of each EDANs curve standard in triplicate to the wells indicated in the 96-well plate map.
8. Using a 1.0-mL or 5.0-mL CombiTip Plus Pipet Tip and the Eppendorf Repeater Plus, draw up the diluted "no peptide" control buffer. If using a 1.0-mL tip, check that the Repeater is set to 5, in order to dispense 100 μL with each click. If using a 5.0-mL tip, check that the Repeater is set to 1, in order to dispense 100 μL with each click.
9. Dispense 100 μL of the "no peptide" control buffer to the appropriate wells.
10. Using a 5.0-mL CombiTip Plus Pipet Tip and the Eppendorf Repeater Plus, draw up the diluted peptide substrate. Check that the Repeater is set to 1, in order to dispense 100 μL with each click.
11. Dispense 100 μL of the diluted peptide substrate to the appropriate well.
12. Place the microplate into the plate holder of the fluorimeter.

Example 7

Example of a Transpiration Membrane or Filter

FIG. 9 is an example of a transpiration membrane or filter. Upon hydrolysis of a blue dye-labeled peptide from the surface of a bead, the blue dye was collected onto a membrane surface by transpiration, a process by which evaporation on the surface of the membrane causes the dye to passively collect on the top surface. In the absence of *Streptococcus pyogenes*, the dye-labeled peptide remained covalently attached to the beads and did not transpire to the top surface of the membrane (FIG. 9A). In the presence of *S. pyogenes*, the peptide and the attached dye were hydrolyzed from the bead and were able to pass through the opaque top membrane, collecting visibly on the top surface (FIG. 9B).

The sensor contains a pile of highly porous microbeads (HyperD CM or Trisacryl beads), tightly packed to operate like an osmotic pump, driving fluid from the sensor bottom pad to the upper, vapor-permeable membrane. The sensor included a bottom glass fiber membrane, a peptide conjugated to carboxy methyl beads with EDC and labeled with blue dye 1 functionalized with a maleimide group, and a top polyethersulfone membrane (Supor, Pall Life Sciences) sealed with an adhesive layer. Briefly, a Millipore Glass Fiber Conjugate Pad (GFCP203000), was cut into a rectangular shape of about 2×4 cm. The Supor 450 or Supor 200 membrane (Pall Corporation, P/N S80710) was cut into a circle of 10 mm diameter and the Supor membrane dimpled to make a shallow (1-2 mm deep) pocket for bead deposition. About one to about 25 conjugate beads (HuperD CM or Trisacryl beads conjugated with a dye-labeled peptide) were dispensed in the Supor pocket and then the two membranes are sealed together using either adhesive tape, RF welding or heat to form a lenticular shaped device that can function as a stand alone sensor or be incorporated into a medical device such as a swab, pick or tooth brush.

This Example is also useful in a two-conjugate system, wherein a second conjugate can amplify the signal released by the first conjugate and be collected onto the membrane surface through transpiration.

Example 8

Optimizing Bead Washing to Optimize Signal to Noise Ratio

Bead Conjugation and Washing
1. Wash 250 μL of CM HyperD beads 2× with 5 mL of 100 mM MES, 200 mM NaCl buffer, pH 6.0 (reaction buffer) for 5 minutes rotating in a 15-mL conical tube. Between and after washes centrifuge the tube and remove the reaction buffer.
2. Add reaction buffer up to a total volume of 1 mL
3. Pipette beads into a conical tube. Centrifuge the tube and remove the excess reaction buffer.
4. Weigh out 30 mg EDC in an eppendorf tube.
5. Weigh out 1.4 mg of H11 crude peptide and dissolve in 1 mL of DMSO.
6. Add 1 mL of reaction buffer to the EDC tube to dissolve the EDC, then immediately add to the conical tube.
7. Add the H11 crude peptide solution to the conical tube.
8. React while rotating at room temperature for 2 hours.
9. Centrifuge and remove and save the reaction buffer for analysis.

10. Weigh out 60 mg of ethanolamine hydrochloride in an eppendorf tube and dissolve in 1 mL of reaction buffer.
11. Weigh out 30 mg EDC in an eppendorf tube.
12. Dissolve EDC in 1 mL reaction buffer. Immediately after EDC is dissolved, add to the conical tube.
13. Add 1 mL of ethanolamine solution to the conical tube.
14. React while rotating at room temperature for 30 minutes.
15. Centrifuge the conical tube and discard the reaction buffers.
16. Add 1 mL of 100 mM CAPs buffer, pH 10.0, with 10% Tween-80 (wash buffer) to the conical tube and transfer the entire volume into a 50-mL conical tube. Centrifuge the tube and discard the supernatant.
17. Add 16 mL of wash buffer to the tube.
18. Rotate the tubes for 2 hours at room temperature.
19. Centrifuge the tubes and discard the supernatant.
20. Repeat steps 18-20 three additional times for a total of 4 wash cycles, 8 hours of washing. Do not centrifuge immediately after the last wash.
21. Remove 4 mL of bead suspension from the tube and pipette into a 15 mL conical tube labeled "8 hours."
22. Centrifuge the 4 mL aliquot and discard the supernatant.
23. Resuspend the bead aliquot in 3 ppm proclin in PBS and store at 4° C.
24. Add 12 mL of wash buffer to the remaining beads and rotate the beads for 2 hours at room temperature.
25. Repeat steps 21-23 and label the aliquot "10 hours."
26. Add 8 mL of wash buffer to the remaining beads and rotate the beads for 2 hours at room temperature.
27. Repeat steps 21-23 and label the aliquot "12 hours."
28. Add 4 mL of wash buffer to the remaining beads and rotate the beads for 2 hours at room temperature.
29. Repeat steps 21-23 and label the aliquot "14 hours."
30. Centrifuge each 15-mL conical tube and remove the buffer.
31. Add 4 mL of 500 mM NaCl to each tube.
32. Rotate the tubes for 30 minutes at room temperature.
33. Centrifuge the tubes and discard the supernatant.
34. Add 4 mL of 500 mM NaCl to each tube.
35. Invert the tubes several times to agitate the beads, then centrifuge the tubes and discard the supernatant.
36. Add 4 mL of 50 mM Tris buffer, pH 8.0, to each tube.
37. Rotate the tubes for 30 minutes at room temperature.
38. Centrifuge the tubes and discard the supernatant.
39. Add 4 mL of 50 mM Tris buffer, pH 8.0, to each tube.
40. Invert the tubes several times to agitate the beads, then centrifuge the tubes and discard the supernatant.
41. Repeat steps 31-32 five additional time for a total of 6 washes.
42. Add 285 µL of 50 mM Tris buffer, pH 8.0, to bring the bead concentration up to 180 mg/mL Transfer the beads to a 2-mL Eppendorf tube and mark the fluid level on the tube.

*Store beads in 3 ppm Proclin overnight between wash steps.

Analysis of Conjugation Methods:
UV-Vis Absorbance of Unreacted Peptide
1. Pipette 500 µL of DMSO and 500 µL of reaction buffer into a quartz crystal cuvette.
2. Set the wavelength to 280 nm. Absorbance at 280 nm is related to peptides and proteins in general.
3. Insert the cuvette into a UV-vis spectrometer and press the "blank" button.
4. Empty the cuvette and clean with DI water.
5. Pipette 1 mL of unreacted peptide into the cuvette.
6. Record the absorbances at 280 nm. Repeat 2 additional times.

In general, the higher the absorbance at both wavelengths, the more peptide is left un-reacted after the conjugation.

Microplate Assay:
1. Prepare standard SpeB protease solutions.
   a. Dilute stock SpeB in 50 mM Tris, pH 8.0, to a concentration of 10 µg/mL
   b. Dilute 10 µL of 10 µg/mL SpeB with 990 µL Tris buffer.
   c. Dilute 20 µL of 100 ng/mL SpeB with 1.980 mL Tris buffer.
2. Pipette 20 µL of beads from each washing time into 6 wells of a 96-well filter plate (see the plate setup below).
3. Pipette 100 µL of 1 ng/mL SpeB solution (100 pg) into 3 of the wells for each washing time (see the plate setup below).
4. Pipette 100 µl of 50 mM Tris pH 8.0 in the remaining 3 of the 6 wells for each washing time (negative control).
5. Express Detect® Microplate Assay for Analysis of Group A *Streptococcus* samples:
   a. Incubate the filter plate for 30 minutes at room temperature on the shaker table.
   b. Centrifuge the 96-well filter plate and collect the filtrate in streptavidin coated wells.
   c. Incubate the streptavidin wells for 60 minutes at room temperature on the shaker table.
   d. Rinse the wells 3 times with TBS-T for 5 minutes each at room temperature on the shaker table.
   e. Add 100 µL of 1:1000 dilution of Ni-NTA-HRP in TBS-T to each well and incubate for 60 minutes at room temperature on the shaker table.
   f. Rinse the wells 3 times with TBS-T for 5 minutes each at room temperature on the shaker table.
   g. Add 100 µL of TMB (equilibrated to room temperature) to each well and immediately transfer the plate to a spectrophotometer plate reader to record the development of color at 650 nm for 5 minutes.
   h. The rate of color development (milliOD/min) will be determined from a linear portion of the data.

|   | 1 | 2 | 3 |
|---|---|---|---|
| A | 8 hrs<br>0 pg | 10 hrs<br>0 pg | 12 hrs<br>100 pg |
| B | 8 hrs<br>0 pg | 10 hrs<br>100 pg | 12 hrs<br>100 pg |
| C | 8 hrs<br>0 pg | 10 hrs<br>100 pg | 14 hrs<br>0 pg |
| D | 8 hrs<br>100 pg | 10 hrs<br>100 pg | 14 hrs<br>0 pg |
| E | 8 hrs<br>100 pg | 12 hrs<br>0 pg | 14 hrs<br>0 pg |
| F | 8 hrs<br>100 pg | 12 hrs<br>0 pg | 14 hrs<br>100 pg |
| G | 10 hrs<br>0 pg | 12 hrs<br>0 pg | 14 hrs<br>100 pg |
| H | 10 hrs<br>0 pg | 12 hrs<br>100 pg | 14 hrs<br>100 pg |

Example 9

Optimization of Control Line Printing

1. Cut the lateral flow strip components:
   Membrane: 2.5 cm×30 cm, Millipore HF180 Nitrocellulose (3)
   Conjugate Pad: 1.3 cm×15 cm, Millipore G041 Glass Fiber (3)
   Sample Pad: 2.0 cm×15 cm, Whatman CF4 (3)
   Absorbent Pads: 3.9 cm×15 cm, Whatman Grade 900 (3)
2. Make the test line solution:
   0.75 mg/mL neutravidin, 5% ethanol in 5 mM sodium acetate, pH 5.3: 150 µL neutravidin stock (10 mg/mL), 1.75 mL sodium acetate, 100 µL ethanol
3. Make the control line solutions:

| Poly-His Solutions | Poly-his Stock (10 mg/mL) | 5 mM Sodium Acetate, pH 6.0 |
|---|---|---|
| A (0.5 mg/mL) | 100 µL | 1.9 mL |
| B (0.25 mg/mL) | 50 µL | 1.95 mL |
| C (0.125 ng/mL) | 25 µL | 1.975 mL |

4. Print the test and control lines on the membranes:
   Sample and control lines are printed at a rate of 1 mL/cm using the BioDot BioJet printing system. Print 1 membrane each using the 3 poly-his solutions. Assign each membrane a lot number.
5. Dry Nanogold onto conjugate pads:
   Dilute the 0.5 µM nanogold solution (in 2 mM borate buffer, pH 7.0) 1:5 for a final concentration of 0.1 µM: Add 1 mL of 0.5 µM nanogold to 4 mL of 2 mM borate buffer, pH 7.0
   Pour the gold solution into a small, shallow dish that is large enough to dip the conjugate pads into.
   Dip each of the conjugate pads into the gold solution and hold up the pads to allow excess solution to run back into the dish.
   Place the dipped conjugate pads onto strips of parafilm and dry in a 40° C. oven for 2 hours.
6. Assemble the lateral flow strips:
   Cut the 30 cm membranes in half and fix half of each membrane to the center adhesive strip on backing cards (15 cm). Fix a gold-coated conjugate pad to the bottom adhesive strip on the backing card. The conjugate pad should overlap the bottom of the membrane slightly (~3 mm). Fix a sample pad to the remaining exposed region of the bottom adhesive strip on the backing card. The sample pad should overlap the bottom of the conjugate pad almost completely (1 cm). Fix an absorbent pad to the top adhesive strip on the backing card. The absorbent pad should overlap the top of the membrane slightly (~3 mm) and hang off the end of the backing card. Cut the cards into individual 5-mm strips.
7. Testing the lateral flow strips:
   Prepare buffer.
   Buffer: 12% saliva, 1% Triton-X100 in 50 mM Tris with 150 mM NaCl, pH 8.0 (10 mL total)
   1.2 mL saliva
   1.0 mL 10% Triton X-100
   7.3 mL 50 mM Tris with 150 mM NaCl, pH 8.0
   Prepare clipped peptide solutions of H11 peptide:
   200 µL sample volumes (3.0 mL total)
   1.5 µL of 1 mg/mL clipped H11+2.99 mL "Buffer."
   The strips will only be tested with 1 amount of clipped peptide. Pipette 200 µL of solutions 1 and Buffer alone as a negative control into the wells of a 96-well microplate according to the layout below. Insert lateral flow strips into the filled wells with conjugate/sample pads down. Record observations regarding the formation of the control line (i.e., quality of the line, intensity of the line, wetting of the line, etc.)

|   | 1 | 2 | 3 | 4 | 5 | 6 |
|---|---|---|---|---|---|---|
| A | A control | B control | C control | A 100 ng | B 100 ng | C 100 ng |

8. Evaluating the line formation
   Select the best quality line formed. If that solution still leads to the slow wetting of the control line, fill in the chart below with the information for the best line and repeat the steps above with the indicated additives (final volume=2.0 mL):

| Poly-His Solutions | Poly-his Stock (10 mg/mL) | 5 mM Sodium Acetate, pH 6.0 | Additive |
|---|---|---|---|
|  |  |  | 0.05% SDS: 100 µL of a 1% solution |
|  |  |  | 0.005% Triton-X 100: 20 µL of a 0.5% solution |

We claim:

1. A device for detecting the presence or absence of a bacterium in a sample, comprising:
   (a) a reaction chamber configured to hold the sample and comprising a first amplifier configured to release a substrate in response to an enzyme produced and/or secreted by the bacterium;
   (b) a membrane;
   (c) a second amplifier in fluid communication with the first amplifier, configured to bind to the released substrate and to produce a signal in the presence of the bacterium; and
   (d) a lateral flow cassette comprising a conjugate pad in fluid communication with the membrane, a lateral flow strip, and a wicking pad;
   wherein the membrane is configured to allow the sample to flow to the conjugate pad and lateral flow strip under conditions that allow the released substrate to bind to the second amplifier, wherein the membrane or conjugate pad filters the first amplifier away from the released substrate such that the first amplifier is prevented from entering the lateral flow strip, and wherein the lateral flow strip is configured to indicate the signal in the presence of the bacterium.

2. The device of claim 1, wherein the signal on the lateral flow strip comprises a pattern.

3. The device of claim 2, wherein the pattern is selected from the group consisting of a line, a cross and a circle.

4. The device of claim 1, wherein the membrane is a size exclusion membrane.

5. The device of claim 4, wherein the size exclusion membrane excludes particles of greater than about 1 micron.

6. The device of claim 4, wherein the size exclusion membrane comprises an absorbent material, a non-absorbent material, an opaque material, a translucent material, or a hollow fiber.

7. The device of claim 1, wherein the device comprises a solid support selected from a toothbrush, a wound dressing, a container for holding body fluids, a disk, a scope, a filter, a lens, a foam, a cloth, a paper, a suture, a dipstick and a swab.

8. The device of claim 1, wherein the bacterium is *Streptococcus pyogenes*.

9. The device of claim 1, wherein the first amplifier comprises a peptide substrate covalently attached to a bead.

10. The device of claim 9, wherein the bead is about 1 to about 100 microns in diameter.

11. The device of claim 1, wherein the substrate comprises an amino acid sequence selected from the group consisting of FLVMFLSG (SEQ. ID. NO.: 1), ILFTLTGCVG (SEQ. ID. NO.: 2) and GSNMYVYNIS (SEQ. ID. NO.: 3).

12. The device of claim 1, wherein the first amplifier further includes one affinity label or at least two different affinity labels.

13. The device of claim 1, wherein the substrate is covalently labeled with a label selected from the group consisting of: affinity tags, spin labels, antigen tags, epitope tags, haptens, enzyme labels, prosthetic groups, fluorescent materials, pH-sensitive materials, chemiluminescent materials, colorimetric components, bioluminescent materials, and radioactive materials.

14. The device of claim 1, wherein the second amplifier is less than about 1 micron in diameter.

15. The device of claim 1, wherein the second amplifier is labeled with an affinity tag.

16. The device of claim 1, wherein the reaction chamber is removable.

17. The device of claim 1, wherein the membrane or conjugate pad includes the second amplifier.

18. The device of claim 1, wherein the membrane further includes the first amplifier.

19. The device of claim 1, further comprising one or more reagents for detecting the enzyme produced and/or secreted by *Streptococcus pyogenes*.

20. The device of claim 1, wherein the sample is incubated with the first amplifier; and wherein the released substrate is incubated with the second amplifier.

21. The device of claim 20, wherein the sample is on a solid support.

22. The device of claim 21, wherein the solid support is a selected from the group consisting of a wound dressing, a container for holding body fluids, a disk, a scope, a filter, a lens, a foam, a cloth, a paper, a suture, a dipstick, a toothbrush, a bead, and a swab.

23. A method for detecting the presence or absence of a bacterium in a sample using a lateral flow device comprising: an enzyme reaction chamber having a membrane, wherein the membrane of the enzyme reaction chamber filters released substrate away from any unreleased substrate; and a lateral flow cassette comprising a conjugate pad in fluid communication with the membrane, a lateral flow strip, a wicking pad, and a flow strip chamber; the method comprising:
   a) contacting the sample with a first amplifier in the enzyme reaction chamber under conditions that result in release of a substrate from the first amplifier in response to an enzyme produced and/or secreted by the bacterium;
   b) collecting the released substrate onto a second amplifier in the enzyme reaction chamber under conditions that allow the released substrate to bind to the second amplifier;
   c) allowing the sample to flow from the enzyme reaction chamber onto the conjugate pad, and
   d) detecting the presence of a signal on the flow strip, wherein the presence of the signal indicates the presence of the bacterium in the sample and absence of a signal on the flow strip indicates the absence of the bacterium in the sample.

24. The device of claim 20, wherein the bacterium is *Streptococcus pyogenes*.

25. The device of claim 20, wherein the substrate comprises an amino acid sequence selected from the group consisting of FLVMFLSG (SEQ. ID. NO.: 1), ILFTLTGCVG (SEQ. ID. NO.: 2) and GSNMYVYNIS (SEQ. ID. NO.: 3).

26. The device of claim 1, wherein the first amplifier is a conjugate capable of being modified by the enzyme which is produced and/or secreted by the bacterium.

27. The device of claim 1, wherein the second amplifier comprises an affinity tag and a color-producing label.

28. The device of claim 1, wherein the second amplifier comprises an NTA-gold labeled particle.

29. The device of claim 1, wherein the lateral flow strip further comprises a charged surface or a binding partner configured to bind specifically to the released peptide.

30. A method for detecting the presence or absence of a bacterium in a sample comprising contacting the sample with the device of claim 1, and detecting the presence or absence of a signal, wherein the presence or absence of the bacterium is detected.

* * * * *